United States Patent
Puhl et al.

(10) Patent No.: US 11,098,075 B2
(45) Date of Patent: Aug. 24, 2021

(54) METHOD FOR PREPARING 2'-O-FUCOSYLLACTOSE

(71) Applicant: BASF SE, Ludwigshafen (DE)

(72) Inventors: Michael Puhl, Hirschberg (DE); Klaus Ditrich, Gönnheim (DE); Andreas Keller, Speyer (DE); Pepa Dimitrova, Worms (DE); Melanie Weingarten, Ratzeburg (DE); Wolfgang Siegel, Limburgerhof (DE)

(73) Assignee: BASF SE, Ludwigshafen am Rhein (DE)

(*) Notice: Subject to any disclaimer, the term of this patent is extended or adjusted under 35 U.S.C. 154(b) by 565 days.

(21) Appl. No.: 15/510,268

(22) PCT Filed: Sep. 11, 2015

(86) PCT No.: PCT/EP2015/070844
§ 371 (c)(1),
(2) Date: Mar. 10, 2017

(87) PCT Pub. No.: WO2016/038192
PCT Pub. Date: Mar. 17, 2016

(65) Prior Publication Data
US 2018/0230176 A1    Aug. 16, 2018

(30) Foreign Application Priority Data
Sep. 12, 2014    (EP) .................... 14184606

(51) Int. Cl.
*C07H 15/26*    (2006.01)
*C07H 3/06*    (2006.01)
(Continued)

(52) U.S. Cl.
CPC .............. *C07H 15/26* (2013.01); *A23L 33/10* (2016.08); *C07H 1/00* (2013.01); *C07H 3/06* (2013.01); *A23V 2002/00* (2013.01)

(58) Field of Classification Search
CPC . C07H 3/06; C07H 15/26; C07H 1/00; A23V 2002/00; A23L 33/10
(Continued)

(56) References Cited

U.S. PATENT DOCUMENTS

| | | |
|---|---|---|
| 5,438,124 A | 8/1995 | Matta et al. |
| 2012/0294840 A1* | 11/2012 | Newburg .............. C07H 3/06 424/93.44 |

FOREIGN PATENT DOCUMENTS

| | | | |
|---|---|---|---|
| WO | WO-2010070616 A2 | 6/2010 | |
| WO | WO 2010/115934 A1 * | 10/2010 | ............... C07H 3/06 |

(Continued)

OTHER PUBLICATIONS

Ott et al, J. Carbohydrate Chem., 2001, 20(7&8), 611-636.*
Ranade et al, J. Carbohydrate Chem., 2013, 32, 1-43.*
Uchiyama et al, Synlett, 1996, 499-501.*
Olah et al, J. Org. Chem., 1979, 44(8), 1247-1251.*
Sassaman et al, J. Org. Chem., 1987, 52, 4314-4319.*
Schelhaas et al, Angew. Chem. Intl. Ed. Engl, 1996, 35, 2057-2083.*
Greene et al, Protective Groups in Organic Synthesis, 2nd Ed, Wiley, 1991, pp. 68-85, 88-90, 98-102, 123-126 and 178-181.*

(Continued)

*Primary Examiner* — Ganapathy Krishnan
(74) *Attorney, Agent, or Firm* — Faegre Drinker Biddle & Reath LLP

(57) ABSTRACT

The present invention relates to a method for preparing 2'-O-fucosyllactose, the 2'-O-fucosyllactose obtainable by this method and the use thereof. The method comprises reacting the persilylated, protected fucose derivatives of the formula (I) below, with at least one tri($C_1$-$C_6$-alkyl)silyl iodide and subsequently reacting the product thus obtained with the compound of the general formula (II), in the presence of a base.

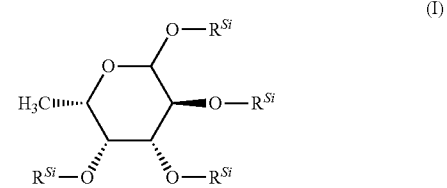

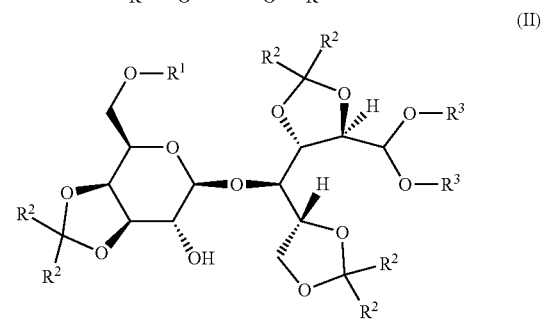

In the formulae (I) and (II), the variables are each defined as follows:
$R^{Si}$ are the same or different and are a residue of the formula $SiR^aR^bR^c$;
$R^1$ is a $C(=O)-R^{11}$ residue or an $SiR^{12}R^{13}R^{14}$ residue,
$R^2$ are the same or different and are $C_1$-$C_8$-alkyl or together form a linear $C_3$-$C_6$-alkanediyl, which is unsubstituted or has 1 to 6 methyl groups as substituents;
$R^3$ are the same or different and are $C_1$-$C_8$-alkyl or together form a linear $C_1$-$C_4$-alkanediyl, which is unsubstituted or has 1 to 6 methyl groups as substituents.

28 Claims, No Drawings

(51) Int. Cl.
C07H 1/00 (2006.01)
A23L 33/10 (2016.01)

(58) Field of Classification Search
USPC .......................................................... 536/7.5
See application file for complete search history.

(56) References Cited

FOREIGN PATENT DOCUMENTS

| WO | WO-2010115934 A1 | 10/2010 |
|---|---|---|
| WO | WO-2010115935 A1 | 10/2010 |
| WO | WO2013/004669 | 7/2012 |
| WO | WO-2012113404 A1 | 8/2012 |
| WO | WO-201348294 A1 | 4/2013 |

OTHER PUBLICATIONS

Abbas, S., et al., "Synthesis of O-α-L-fucopyranosyl-(1→2)-O-β-D-galactopyranosyl-(1→4)-D-glucopyranose (2'-O-α-L-fucopyranosyl-lactose", Carbohydrate Research, vol. 88, No. 1, (1981), pp. 51-60.

Fernandez-Mayoralas, A., et al., "Synthesis of 3- and 2'-fucosyl-lactose and 3,2'-difucosyl-lactose from partially benzylated lactose derivatives", Carbohydrate Research, vol. 154, No. 1, (1986), pp. 93-101.

International Search Report for PCT/EP2015/070844 dated Nov. 10, 2015.

Izumi, M., et al., "Synthesis of 5-Thio-L-fucose-Containing Disaccharides, as Sequence-Specific Inhibitors, and 2'-Fucosyllactose, as a Substrate of α-L-Fucosidases", Journal of Organic Chemistry, vol. 62, No. 4, (1997), pp. 992-998.

Jain, R., et al., "A convienient synthesis of O-α-L-fucopyranosyl-(1→2)-O-β-D-galactopyranosyl-(1→4)-D-glucopyranose (2'-O-α-L-fucopyranosyllactose)", Carbohydrate Research, vol. 212, No. , (1991), pp. c1-c3.

Jantscher-Krenn, E., et al., "Human milk oligosaccharides and their potential benefits for the breast-fed neonate", Minerva Pediatrica, vol. 64, No. 1, (2012), pp. 83-99.

Kogelberg, H., et al., Sulfation of O-isopropylidenated lactose derivatives at the 2'-position induces an unusual $^{3,0}$B-boat conformation of the D-galactosyl residue, Carbohydrate Research, vol. 201, No. 2, (1990), pp. 161-173.

Morrow, A., et al., "Human milk oligosaccharides are associated with protection against diarrhea in breast-fed infants", The Journal of Pediatrics, vol. 145, No. 3, (2004), pp. 297-303.

Pereira, C., et al., "Synthesis of human milk oligosaccharides: 2'- and 3'-fucosyllactose", Heterocycles, vol. 84, No. 1, (2012), pp. 637-655.

Weichert, S., et al., "Bioengineered 2'-fucosyllactose and 3-fucosyllactose inhibit the adhesion of *Pseudomonas aeruginosa* and enteric pathogens to human intestinal and respiratory cell lines", Nutrition Research, vol. 33, No. 10, (2013), pp. 831-838.

Written Opinion of the International Searching Authority for PCT/EP2015/070844 dated Nov. 10, 2015.

Sevrain, C., "Organic & Biomolecular Chemistry", DiGalactosyl-Glycero-Ether Lipid: synthetic approaches and evaluation as SK3 channel inhibitort, 2013, vol. 11, pp. 4479-4487.

* cited by examiner

METHOD FOR PREPARING 2'-O-FUCOSYLLACTOSE

CROSS-REFERENCE TO RELATED APPLICATIONS

This application is a national stage application (under 35 U.S.C. § 371) of PCT/EP2015/070844, filed Sep. 11, 2015, which claims benefit of European Application No. 14184606.3, filed Sep. 12, 2014, both of which are incorporated herein by reference in their entirety.

The present invention relates to a method for preparing 2'-O-fucosyllactose, the 2'-O-fucosyllactose obtainable by this method and the use thereof.

BACKGROUND OF THE INVENTION

2'-O-Fucosyllactose (CAS-No.: 41263-94-9: α-L-fucopyranosyl)-(1→2)-O-ß-D-galactopyranosyl-(1→4)-D-glucopyranose) is an oligosaccharide, which is found in relatively large quantities in breast milk. It has been variously reported that the 2'-O-fucosyllactose present in breast milk causally reduces the risk of infection in newborns who are breast fed (see e.g. Weichert et al, Nutrition Research, 33 (2013), Volume 10, 831-838; Jantscher-Krenn et al, Minerva Pediatr. 2012, 64 (1) 83-99; Morrow et al, J. Pediatr. 145 (2004) 297-303). 2'-O-fucosyllactose is therefore of particular interest as a constituent of food supplements, particularly as additive for humanized milk products, particularly for infant nutrition.

The preparation of 2'-O-fucosyllactose by classical chemical or biochemica means has been variously described in the literature (see e.g. Carbohydrate Res. 88(1) (1981) 51, Carbohydrate. Res. 154 (1986) 93-101, Carbohydrate. Res. 212 (1991) C1-C3, J. Org. Chem. (1997) 62, 992, Heterocycles 84(1) (2012) 637, U.S. Pat. No. 5,438,124, WO 2010/115934, WO 2010/115935, WO 2010/070616, and WO 2012/113404. The chemical preparation is typically based on fucosylation of suitably protected acceptors, i.e. lactose derivatives partially protected, unprotected at the 2-position, which bear a thioalkyl group, an alkenyloxy group, a trichloroacetimidate or a bromine atom in place of the anomeric OH group, e.g. 4-O-(6-O-acetyl-3,4-isopropylidene-ß-D-galactopyranosyl)-2,3;5,6-bis-O-isopropylidene-D-glucose dimethylacetal, by using activated fucosyl donors such as methyl 1-thio-2,3,4-tri-O-benzyl-ß-L-fucopyranoside, methyl 3,4-O-isopropylidene-2-O-(4-methoxybenzyl)-1-thio-L-fucopyranoside, pentenyl 3,4-O-isopropylidene-2-O-(4-methoxybenzyl)-ß-L-fucopyranoside, phenyl 1-thio-2,3,4-tri-O-benzyl-ß-L-fucopyranoside, 2,3,4-tri-O-benzyl-ß-L-fucopyranosyl bromide, or 2,3,4-tri-O-benzyl-ß-L-fucopyranosyl trichloracetimidate (with respect to fucose donors see the literature cited above and Tetrahedron Lett. 31 (1990) 4325). A disadvantage is the complex, generally multistage preparation, of the fucose donors. Another disadvantage is found to be that the benzyl protecting groups of the fucosylating reagents must be removed by hydrogenolysis using heavy metal-containing catalysts, which leads to impurities in the product which are difficult to remove and which are not acceptable for foodstuff.

For instance, R. K. Jain et al., Carbohydrate Research, 212 (1991), pp. C1-C3 describe a route for the preparation of 2'-O-fucosyllactose by fucosylation of 4-O-(6-O-acetyl-3,4-isopropylidene-ß-D-galactopyranosyl)-2,3;5,6-bis-O-isopropylidene-D-glucose dimethylacetal using methyl 3,4-O-isopropylidene-2-O-(4-methoxybenzyl)-1-thio-ß-L-fucopyranoside or pentyl 3,4-O-isopropylidene-2-O-(4-methoxybenzyl)-ß-L-fucopyranoside as fucosylating reagents. These fucosylating reagents are, however, complex to prepare. A similar synthesis is described in J. Org. Chem. 1997, 62, 992.

WO 2010/115934 and WO 2010/115935 describe the preparation of 2-fucosyllactose using 2-O-benzylated fucosyl donors. The fucosyl donors are complex to prepare and still have benzyl groups which have to be removed by hydrogenolysis. A similar method is known from WO 2010/070616.

WO 2012/113404 describes, inter alia, O-protected fucosyl phosphites, which may be used as fucosyl donors in glycosylations. Here also, the 2,3,4-O-protected fucose derivatives must first be prepared in multistage reactions which are subsequently reacted with phosphorus(III) trichloride and a phenol to the corresponding fucosyl phosphite.

In summary, it can be stated that the methods known to date for preparing 2'-O-fucosyllactose are complex and therefore not economical. Moreover, reagents are used, which are problematic from an ecotoxicological viewpoint. What is more, the resulting 2'-O-fucosyllactose contains impurities which cannot be removed completely, such as transition material and aromatics from the hydrogenolytic removal of the benzyl protecting groups, and also undesirable trisaccharides, such as the ß-isomer of 2'-O-fucosyllactose, namely ß-L-fucopyranosyl-(1→2)-O-ß-D-galactopyranosyl-(1→4)-D-glucopyranose. These impurities are particularly problematic, if 2'-O-fucosyllactose is used in human nutrition, in particular infant nutrition.

SUMMARY OF THE INVENTION

It is an object of the present invention to provide a method for preparing 2'-O-fucosyllactose which does not have the problems of the prior art. The method should in particular allow the use of starting materials that can be easily prepared, particularly readily available fucosyl donors. The method should further ensure good yields and good stereoselectivity in the fucosylation. In addition, the method should be suitable so as to avoid the removal of any protecting groups by hydrogenolysis over transition metal catalysts.

It has been found that reacting the persilylated, protected fucose derivatives of the formula (I) below, in particular the α-anomers of formula (I-α) below:

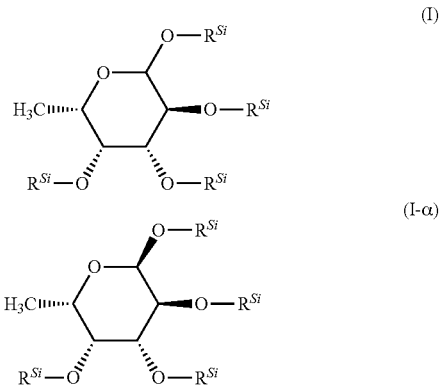

where $R^{Si}$ is a residue of the formula $SiR^aR^bR^c$, where $R^a$, $R^b$ and $R^c$ are the same or different and are selected from $C_1$-$C_8$-alkyl, $C_3$-$C_8$-cycloalkyl, phenyl and $C_3$-$C_8$-cycloalkyl-$C_1$-$C_4$-alkyl, with a tri($C_1$-$C_6$-alkyl)silyl iodide and subsequently reacting the fucose donor thus obtained, the corresponding iodide, with a suitable lactose acceptor, namely the compound of the general formula (II) defined in more detail below, in the presence of at least one base, a corresponding, protected 2'-O-fucosyllactose derivative of the general formula (III) is obtained in good yields and high selectivity, which can then be deprotected in a manner known per se to obtain 2'-O-fucosyllactose, without a hydrogenation step being required.

Accordingly, the invention firstly relates to a method for preparing 2'-O-fucosyllactose, comprising the steps of:

a) reacting the protected fucose of the general formula (I), in particular the α-anomer of formula (I-α) below:

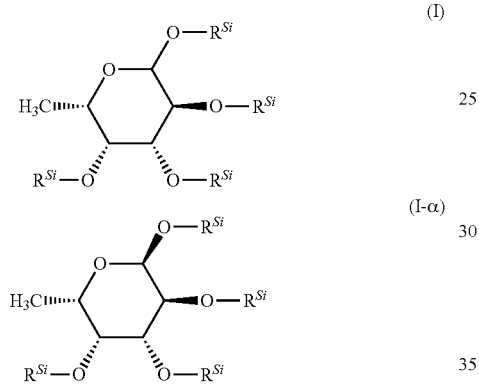

where $R^{Si}$ is a residue of the formula $SiR^aR^bR^c$, where $R^a$, $R^b$ and $R^c$ are the same or different and are selected from $C_1$-$C_8$-alkyl, $C_3$-$C_8$-cycloalkyl, phenyl and $C_3$-$C_8$-cycloalkyl-$C_1$-$C_4$-alkyl;

with a compound of the general formula (II)

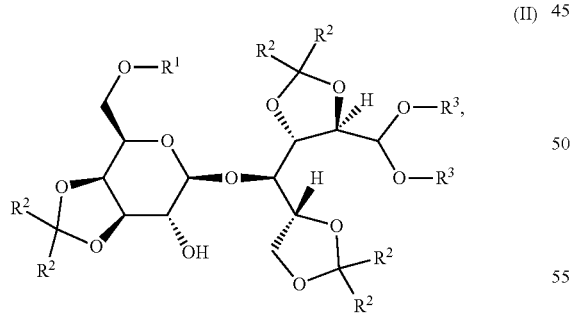

where $R^1$ is a C(=O)—$R^{11}$ residue or an $SiR^{12}R^{13}R^{14}$ residue, in which $R^{11}$ is hydrogen, $C_1$-$C_8$-alkyl, $C_1$-$C_8$-haloalkyl, $C_3$-$C_8$-cycloalkyl, $C_3$-$C_8$-cycloalkyl-$C_1$-$C_4$-alkyl or phenyl, wherein said phenyl is unsubstituted or optionally has 1 to 5 substituents selected from halogen, CN, $NO_2$, $C_1$-$C_4$-alkyl, $C_1$-$C_4$-alkoxy, $C_1$-$C_4$-haloalkyl and $C_1$-$C_4$-alkoxy, and $R^{12}$, $R^{13}$ and $R^{14}$ are the same or different and are selected from $C_1$-$C_8$-alkyl, $C_3$-$C_8$-cycloalkyl, phenyl and $C_3$-$C_8$-cycloalkyl-$C_1$-$C_4$-alkyl;

$R^2$ may be the same or different and are $C_1$-$C_8$-alkyl or 2 $R^2$ residues attached to the same carbon atom together form a linear $C_3$-$C_6$-alkanediyl, which is unsubstituted or has 1 to 6 methyl groups as substituents;

$R^3$ may be the same or different and are $C_1$-$C_8$-alkyl or together form a linear $C_1$-$C_4$-alkanediyl, which is unsubstituted or has 1 to 6 methyl groups as substituents;

b) deprotecting the coupling product of the general formula (III) obtained in step a)

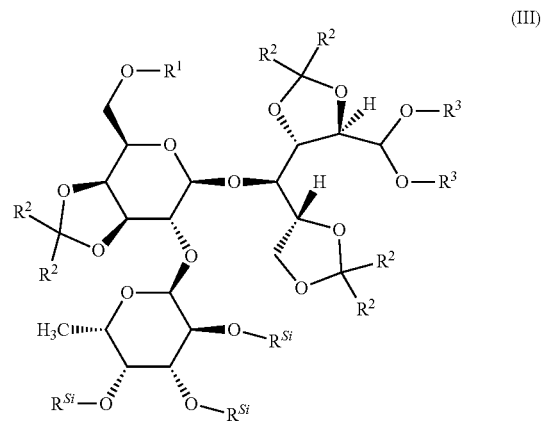

where $R^{Si}$, $R^1$, $R^2$ and $R^3$ are as defined above;

to obtain 2'-O-fucosyllactose;

wherein step a) comprises a.1) treatment of the protected fucose of the general formula (I) with a tri($C_1$-$C_8$-alkyl)silyl iodide and a.2) reaction of the product obtained in step a.1) with the compound of the formula (II) in the presence of at least one base.

The invention further relates to the protected and partially protected 2'-O-fucosyllactose derivatives of the general formulae (IIIa), (IIIb), (IIIc) und (IV):

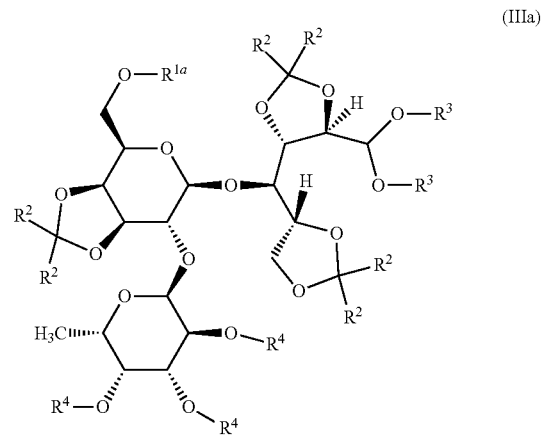

-continued (IIIb)
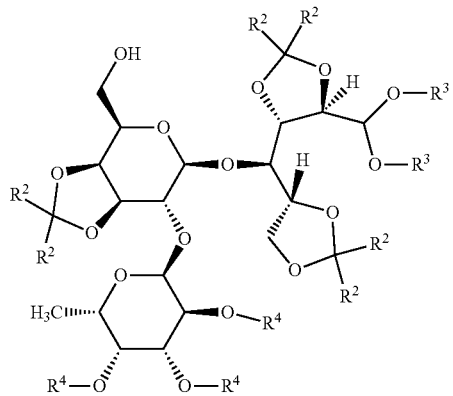

(IIIc)
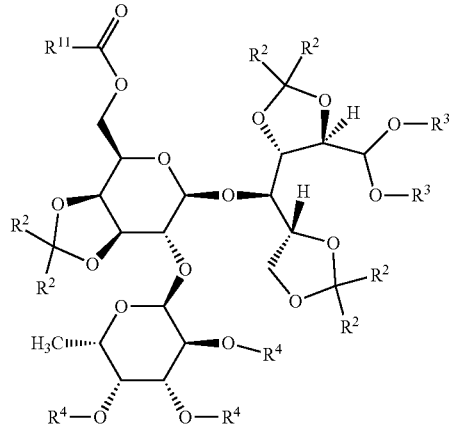

(IV)
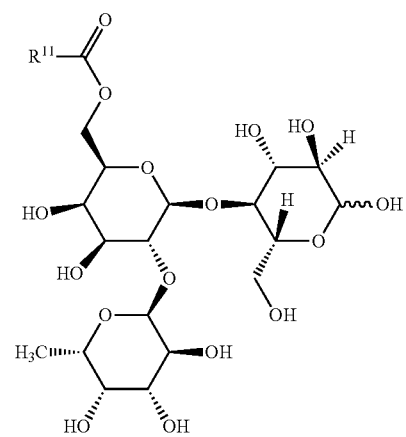

in which:
R$^{1a}$ in formula (IIIa) is an SiR$^{12}$R$^{13}$R$^{14}$ residue, where R$^{12}$, R$^{13}$ and R$^{14}$ are the same or different and are selected from C$_1$-C$_8$-alkyl, C$_3$-C$_8$-cycloalkyl, phenyl and C$_3$-C$_8$-cycloalkyl-C$_1$-C$_4$-alkyl;

R$^2$ in the formulae (IIIa), (IIIb) and (IIIc) are the same or different and are C$_1$-C$_8$-alkyl or two R$^2$ residues attached to the same carbon atom together form a linear C$_3$-C$_6$-alkanediyl, which is unsubstituted or has 1 to 6 methyl groups as substituents;

R$^3$ in the formulae (IIIa), (IIIb) and (IIIc) may be the same or different and are C$_1$-C$_8$-alkyl or together form a linear C$_1$-C$_4$-alkanediyl, which is unsubstituted or has 1 to 6 methyl groups as substituents;

R$^4$ in the formulae (IIIa), (IIIb) and (IIIc) are the same or different and are hydrogen or an SiR$^a$R$^b$R$^c$ residue, where R$^a$, R$^b$ and R$^c$ are the same or different and are selected from C$_1$-C$_8$-alkyl, C$_3$-C$_8$-cycloalkyl, phenyl and C$_3$-C$_8$-cycloalkyl-C$_1$-C$_4$-alkyl;
and R$^{11}$ in the formulae (IIIc) and (IV) is hydrogen, C$_1$-C$_8$-alkyl, C$_1$-C$_8$-haloalkyl, C$_3$-C$_8$-cycloalkyl, C$_3$-C$_8$-cycloalkyl-C$_1$-C$_4$-alkyl or phenyl, wherein said phenyl is unsubstituted or optionally has 1 to 5 substituents selected from halogen, CN, NO$_2$, C$_1$-C$_4$-alkyl, C$_1$-C$_4$-alkoxy, C$_1$-C$_4$-haloalkyl and C$_1$-C$_4$-haloalkoxy.

The invention further relates to the partially protected lactose derivatives of the general formula (II), where R$^1$ is an SiR$^{12}$R$^{13}$R$^{14}$ residue, where R$^{12}$, R$^{13}$ and R$^{14}$ are the same or different and are selected from C$_1$-C$_8$-alkyl, C$_3$-C$_8$-cycloalkyl, phenyl and C$_3$-C$_8$-cycloalkyl-C$_1$-C$_4$-alkyl. These are described below by the formula (IIa):

(IIa)
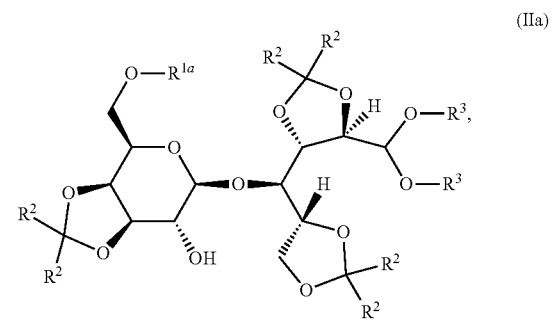

where R$^{1a}$ is an SiR$^{12}$R$^{13}$R$^{14}$ residue, where R$^{12}$, R$^{13}$ and R$^{14}$ are as previously defined and R$^2$ and R$^3$ are as defined for the formulae (II), (III), (IIIa), (IIIb) and (IIIc).

The inventive method is linked to a series of advantages. A complex preparation of fucosyl donors can be avoided, since the compound of the formula (I) may be prepared in one step from fucose. The method affords the primary coupling product of the formula (III) in good yields and good stereoselectivity relative to the glycosylation. The removal of the protecting groups in the compound of the formula (III) is possible under mild hydrolysis conditions, without the need for a hydrogenolysis over transition metal catalysts. The resulting intermediates of the formula (III), particularly of the formulae (IIIa), (IIIb) and (IIIc), are stable, in particular stable during storage, and may be purified. In addition, the method can readily be carried out on a relatively large scale. A further advantage is that the 2'-O-fucosyllactose obtainable by the method according to the invention, in comparison to the known 2'-O-fucosyllactose, does not comprise, or only comprises in much lower fractions, those impurities which cannot be removed, the heavy metals and heavy metal compounds resulting from a hydrogenation for example, and also alkyl aromatic compounds which are formed by hydrogenation of the protecting groups. Furthermore, by the method of the invention the undesirable ß-isomer is not formed or only formed to a very low extent, which is much lower than the amount of ß-isomer formed in the methods of prior art. Indeed, by the reaction of the compound of formula (I) with the compound of formula (II), the undesirable ß-isomer of the compound of formula (III) is formed in such a low amount that the molar ratio of ß-isomer (III-ß) to α-isomer (III-α) does not exceed 1:25, and is in particular in the range of 1:35 to 1:40. Thus, the method of the invention allows for producing 2'-O-fucosyllactose which, optionally after further purification, contains the desired 2'-O-fucosyllactose containing less than 1% by weight, in particular less than 0.5% by weight, of the undesirable ß-isomer.

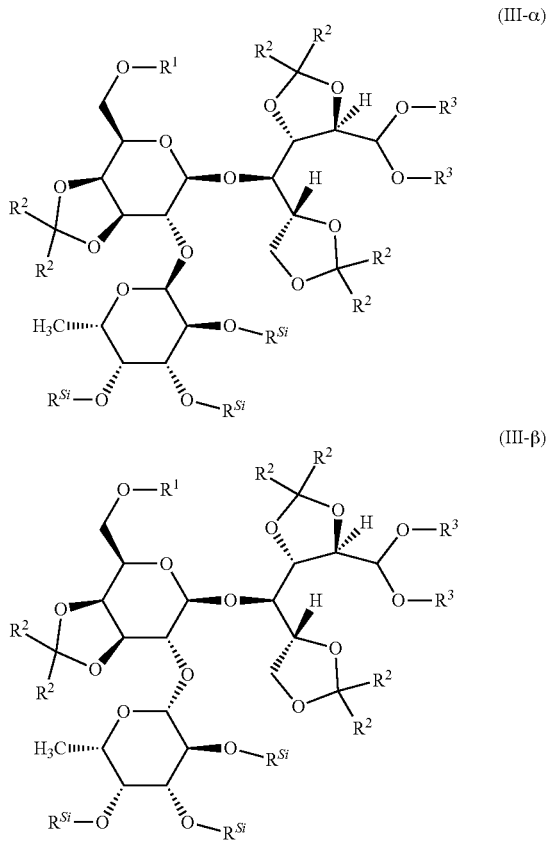

The method and the reactants of the formula (IIa) obtained by the method and intermediate products of the formulae (IIIa), (IIIb), (IIIc) and (IV) are, therefore, particularly suitable for preparing 2'-O-fucosyllactose. Accordingly, the present invention also relates to the use of compounds of the general formula (IIIa) for preparing 2'-O-fucosyllactose and also the use of compounds of the general formulae (IIIa), (IIIb), (IIIc) or (IV) for preparing 2'-O-fucosyllactose.

The quality of the 2'-O-fucosyllactose obtained by the method according to the invention renders it particularly suitable for preparing foodstuffs. Accordingly, the present invention also relates to
- the 2'-O-fucosyllactose obtainable by the method described here;
- the 2'-O-fucosyllactose prepared by using at least one of the compounds of the general formulae (IIa), (IIIa), (IIIb), (IIIc) or (IV);
- the use of the 2'-O-fucosyllactose obtainable by the method described here in foodstuffs or as food additive;
- the use of the 2'-O-fucosyllactose prepared by using at least one of the compounds of the general formulae (IIa), (IIIa), (IIIb), (IIIc) or (IV) in foodstuffs or as food additive;
- a method for preparing foodstuffs comprising the preparation of 2'-O-fucosyllactose from at least one of the compounds of the general formulae (IIa), (IIIa), (IIIb), (IIIc) or (IV) and formulation of the 2'-O-fucosyllactose thus obtainable in a foodstuff;
- a foodstuff or food additive, comprising 2'-O-fucosyllactose, obtainable by a method as described herein and at least one carrier suitable for foodstuff.

DETAILED DESCRIPTION OF THE INVENTION

In the context of the present invention, the terms used generically are defined as follows:

The prefix $C_x$-$C_y$ denotes the number of possible carbon atoms in the particular case.

The term "halogen" in each case denotes fluorine, bromine, chlorine or iodine, specifically fluorine, chlorine or bromine.

The term "$C_1$-$C_4$-alkyl" denotes a linear or branched alkyl residue comprising 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term "$C_1$-$C_8$-alkyl" denotes a linear or branched alkyl residue comprising 1 to 8 carbon atoms. Examples, in addition to the residues mentioned for $C_1$-$C_4$-alkyl, are n-pentyl, n-hexyl, n-heptyl, n-octyl, 2-pentyl, 2-hexyl, 2-heptyl, 2-octyl, 3-pentyl, 3-hexyl, 3-heptyl, 3-octyl, 2,2-dimethylpropyl, 2-methylbutyl, 3-methylbutyl, 2-ethylbutyl, 3-ethylbutyl, 2-methylpentyl, 3-methylpentyl, 4-methylpentyl, 2-ethylpentyl, 3-ethylpentyl, 4-ethylpentyl, 2-ethylhexyl and positional isomers thereof.

The term "$C_1$-$C_8$-haloalkyl" denotes a linear or branched alkyl residue comprising 1 to 8 carbon atoms, particularly 1 to 4 carbon atoms ($C_1$-$C_4$-haloalkyl), in which one or more or all hydrogen atoms have been replaced by halogen atoms, in particular by fluorine or chlorine atoms. Examples for this purpose are chloromethyl, dichloromethyl, trichloromethyl, fluoromethyl, difluoromethyl, trifluoromethyl, chlorofluoromethyl, dichlorofluoromethyl, chlorodifluoromethyl, 2,2-difluoroethyl, 2,2,2-trifluoroethyl, 1,1,2,2-tetrafluoroethyl, pentafluoroethyl, 2,2-difluoropropyl, 3,3-difluoropropyl, 3,3,3-trifluoropropyl, 2,2,3,3,3-pentafluoropropyl, heptafluoropropyl, and the like.

The term "$C_1$-$C_4$-alkoxy" denotes straight-chain or branched saturated alkyl groups comprising 1 to 4 carbon atoms which are bonded via an oxygen atom. Examples of $C_1$-$C_4$-alkoxy are methoxy, ethoxy, n-propoxy, 1-methylethoxy (isopropoxy), n-butoxy, 1-methylpropoxy (sec-butoxy), 2-methylpropoxy (isobutoxy) and 1,1-dimethylethoxy (tert-butoxy).

The term "$C_1$-$C_4$-haloalkoxy" denotes straight-chain or branched saturated haloalkyl groups comprising 1 to 4 carbon atoms which are bonded via an oxygen atom. Examples in this case are fluoromethoxy, difluoromethoxy, trifluoromethoxy, 1-fluoroethoxy, 2-fluoroethoxy, 2,2-difluoroethoxy, 2,2,2-trifluoroethoxy, 1,1,2,2-tetrafluoroethoxy, pentafluoroethoxy, 3,3,3-trifluoroprop-1-oxy, 1,1,1-trifluoroprop-2-oxy, 1-fluorobutoxy, 2-fluorobutoxy, 3-fluorobutoxy, 4-fluorobutoxy and the like.

The term "$C_3$-$C_8$-cycloalkyl" denotes a cyclic, saturated hydrocarbyl residue comprising 3 to 8 carbon atoms. Examples are cyclopropyl, cyclobutyl, cyclopentyl, cyclohexyl, cycloheptyl and cyclooctyl.

The term "$C_3$-$C_8$-cycloalkyl-$C_1$-$C_4$-alkyl" denotes a linear or branched alkyl residue comprising 1 to 4 carbon atoms, in which one hydrogen atom has been replaced by $C_3$-$C_8$-cycloalkyl, as defined above.

The term "linear $C_1$-$C_4$-alkanediyl" denotes a linear, divalent hydrocarbyl residue having 1 to 4 carbon atoms, such as methylene, ethane-1,2-diyl, propane-1,3-diyl, and butane-1,4-diyl.

The term "linear $C_3$-$C_6$-alkanediyl" denotes a linear, divalent hydrocarbyl residue having 3 to 6 carbon atoms, such as propane-1,3-diyl, butane-1,4-diyl, pentane-1,5-diyl and hexane-1,6-diyl.

The term "foodstuff" or "food" denotes compositions and formulations which are intended and suitable as nutrition for mammals, particularly human beings. In the context of the present invention, they include both compositions based on naturally-occurring products, e.g. dairy products, and also artificially prepared formulations, for example, for dietary or medicinal nutrition, which can be used directly or optionally have to be converted into a ready-to-use formulation before use by addition of liquid.

The term "food additive" denotes substances which are mixed with the foodstuff to achieve chemical, physical or also physiological effects.

With respect to the method according to the invention and the compounds of the formulae (II), (IIa), (III), (IIIa), (IIIb), (IIIb'), (IIIc) and (IIIc'), the variables $R^2$ within one formula preferably have the same definition in each case. $R^2$ is in particular $C_1$-$C_4$-alkyl and especially methyl or two $R^2$ residues attached to the same carbon atom are together 1,5-pentanediyl and thus form a cyclohexane-1,1-diyl residue with the carbon atom to which they are attached. All $R^2$ residues are especially methyl.

With respect to the method according to the invention and the compounds of the formulae (II), (IIa), (III), (IIIa), (IIIb), (IIIb'), (IIIc) and (IIIc'), the variables $R^3$ within one formula preferably have the same definition in each case. $R^3$ is particularly $C_1$-$C_4$-alkyl and especially methyl.

With respect to the method according to the invention and the compounds of the formulae (IIIa), (IIIb) and (IIIc), the variables $R^4$ within one formula preferably have the same definition in each case. $R^4$ is particularly hydrogen or tri($C_1$-$C_4$-alkyl)silyl, especially hydrogen or trimethylsilyl, i.e. in the $SiR^aR^bR^c$ residue, the residues $R^a$, $R^b$ and $R^c$ are the same or different and are particularly $C_1$-$C_4$-alkyl, especially methyl. In the compounds of the formula (IIIa), $R^4$ is particularly tri($C_1$-$C_4$-alkyl)silyl, especially trimethylsilyl. In the compounds of the formula (IIIb), $R^4$ is particularly hydrogen.

With respect to the method according to the invention and the compounds of the formulae (I) and (II), the variables $R^{Si}$ within one formula preferably have the same definition in each case. $R^{Si}$ is particularly hydrogen or tri($C_1$-$C_4$-alkyl) silyl, especially hydrogen or trimethylsilyl, i.e. in the $SiR^aR^bR^c$ residue, the residues $R^a$, $R^b$ and $R^c$ are the same or different and are particularly $C_1$-$C_4$-alkyl, especially methyl.

A first embodiment relates to a method, where in the compounds of the formulae (II) and (II), the $R^1$ residue is an $SiR^{12}R^{13}R^{14}$ residue, particularly tri($C_1$-$C_4$-alkyl)silyl, especially trimethylsilyl, i.e. in the $SiR^{12}R^{13}R^{14}$ residue, the residues $R^{12}$, $R^{13}$ and $R^{14}$ are the same or different and are particularly $C_1$-$C_4$-alkyl, especially methyl.

Accordingly, in the formulae (IIa) and (IIIa), the $R^{1a}$ is tri($C_1$-$C_4$-alkyl)silyl, especially trimethylsilyl.

A second preferred embodiment relates to a method, in which, in the compounds of the formulae (II) and (III), the $R^1$ residue is a $C(=O)$—$R^{11}$ residue, where $R^{11}$ is as defined above and is particularly hydrogen, $C_1$-$C_4$-alkyl, $C_1$-$C_4$-haloalkyl or phenyl and especially methyl, tert-butyl or phenyl. Accordingly, in the formulae (IIIc), (IIIc') and (IV), the $R^{11}$ residue is preferably hydrogen, $C_1$-$C_4$-alkyl, $C_1$-$C_4$-haloalkyl or phenyl and especially methyl, tert-butyl or phenyl. In certain embodiments of the invention, $R^{11}$ differs from methyl. In special groups of embodiments, $R^{11}$ is methyl. In further special groups of embodiments, $R^{11}$ is tert-butyl.

An example of a particularly preferred compound of the formula (I) is the compound of the formula (I) where all $R^{Si}$ residues are trimethylsilyl.

In the method of the invention, the compound of formula (I) is usually employed in the form of its α-anomer (I-α). It is also possible to the compound of formula (I) as its ß-anomer (I-ß) as a mixture of the α-anomer (I-α) and the ß-anomer (I-ß). The compound of formula (I) is usually employed in a form consisting essentially of its α-anomer (I-α), i.e. the ratio of the α-anomer to the ß-anomer is at least 8:1 or at least 9:1. However, the ratio does not noticeably affect the formation of the desired isomer of (III).

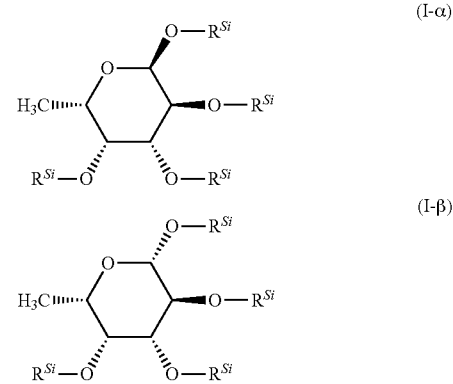

An example of a particularly preferred compound of the formula (III) is the compound of the formula (II) where all $R^2$ residues are methyl, all $R^3$ residues are methyl and $R^1$ is trimethylsilyl. This compound is also an example of the compounds of the formula (IIa).

An example of a further particularly preferred compound of the formula (II) is also the compound of the formula (II) where all $R^2$ residues are methyl, all $R^3$ residues are methyl and $R^1$ is acetyl.

Another example of a further particularly preferred compound of the formula (II) is also the compound of the formula (II) where all $R^2$ residues are methyl, all $R^3$ residues are methyl and $R^1$ is benzoyl.

Another example of a further particularly preferred compound of the formula (II) is also the compound of the formula (II) where all $R^2$ residues are methyl, all $R^3$ residues are methyl and $R^1$ is pivaloyl, i.e. $C(=O)$—$C(CH_3)_3$.

Examples of particularly preferred compounds of the formula (III) are the compound of the formula (III), where all $R^2$ residues are methyl, all $R^3$ residues are methyl, all $R^{Si}$ residues are trimethylsilyl and $R^1$ is trimethylsilyl;

the compound of the formula (III), where all $R^2$ residues are methyl, all $R^3$ residues are methyl, all $R^{Si}$ residues are trimethylsilyl and $R^1$ is acetyl;

the compound of the formula (III), where all $R^2$ residues are methyl, all $R^3$ residues are methyl, all $R^{Si}$ residues are trimethylsilyl and $R^1$ is pivaloyl.

Examples of particularly preferred compounds of the formula (IIIa) are the compound of the formula (IIIa), where all $R^2$ residues are methyl, all $R^3$ residues are methyl, all $R^4$ residues are trimethylsilyl and $R^{1a}$ is trimethylsilyl; and the compound of the formula (IIIa), where all $R^2$ residues are methyl, all $R^3$ residues are methyl, all $R^4$ residues are hydrogen and $R^{19}$ is trimethylsilyl.

Examples of particularly preferred compounds of the formula (IIIb) are the compound of the formula (IIIb), where all $R^2$ residues are methyl, all $R^3$ residues are methyl and all $R^4$ residues are trimethylsilyl;

the compound of the formula (IIIb), where all $R^2$ residues are methyl, all $R^3$ residues are methyl and all $R^4$ residues are hydrogen.

Examples of particularly preferred compounds of the formula (IIIc) are the compound of the formula (IIIc), where all $R^2$ residues are methyl, all $R^3$ residues are methyl, all $R^4$ residues are trimethylsilyl and $R^{11}$ is hydrogen;

the compound of the formula (IIIc), where all $R^2$ residues are methyl, all $R^3$ residues are methyl, all $R^4$ residues are hydrogen and $R^{11}$ is hydrogen;

the compound of the formula (IIIc), where all $R^2$ residues are methyl, all $R^3$ residues are methyl, all $R^4$ residues are trimethylsilyl and $R^{11}$ is methyl;

the compound of the formula (IIIc), where all $R^2$ residues are methyl, all $R^3$ residues are methyl, all $R^4$ residues are hydrogen and $R^{11}$ is methyl;

the compound of the formula (IIIc), where all $R^2$ residues are methyl, all $R^3$ residues are methyl, all $R^4$ residues are trimethylsilyl and $R^{91}$ is phenyl;

the compound of the formula (IIIc), where all $R^2$ residues are methyl, all $R^3$ residues are methyl, all $R^4$ residues are hydrogen and $R^{11}$ is phenyl;

the compound of the formula (IIIc), where all $R^2$ residues are methyl, all $R^3$ residues are methyl, all $R^4$ residues are trimethylsilyl and $R^1$ is tert-butyl;

the compound of the formula (IIIc), where all $R^2$ residues are methyl, all $R^3$ residues are methyl, all $R^4$ residues are hydrogen and $R^1$ is tert-butyl.

Examples of particularly preferred compounds of the formula (IV) are the compound of the formula (IV), where $R^{11}$ is methyl;
the compound of the formula (IV), where $R^{11}$ is ethyl;
the compound of the formula (IV), where $R^{11}$ is phenyl;
the compound of the formula (IV), where $R^{11}$ is tert-butyl.

Step a) of the method according to the invention comprises the treatment of the protected fucose of the general formula (I) with at least one tri($C_1$-$C_6$-alkyl)silyl iodide. In this case, the compound of the formula (I) is selectively converted to the corresponding iodide of the general formula (I'):

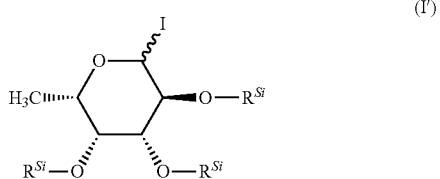

This reaction is also referred to as step a.1) below. The reaction product obtained is then reacted with the compound of the formula (II), wherein the reaction takes place in the presence of at least one base in order to scavenge the hydrogen iodide optionally formed in the reaction (step a.2).

The tri($C_1$-$C_6$-alkyl)silyl iodide preferably used is trimethylsilyl iodide.

The tri($C_1$-$C_6$-alkyl)silyl iodide is preferably used in an amount of 0.8 mol to 1.4 mol or 0.8 mol to 1.2 mol, particularly in an amount of 0.9 to 1.1 mol, especially in an amount of 0.9 to 1 mol per mole of the compound of the formula (I).

The tri($C_1$-$C_6$-alkyl)silyl iodide, particularly trimethylsilyl iodide, can be used as such. The tri($C_1$-$C_6$-alkyl)silyl iodide, particularly trimethylsilyl iodide, can also be prepared in situ.

For example, in situ preparation of tri($C_1$-$C_6$-alkyl)silyl iodide can be achieved by treatment of the corresponding tri($C_1$-$C_6$-alkyl)silyl chloride with an iodide salt, particularly an alkali metal iodide, such as lithium iodide, potassium iodide or sodium iodide. Suitable methods for this are known, e.g. from Synthesis 1983, p. 459, Synthesis 1979, p. 740, Synthesis 1981, p. 67, Chem. Ber. 1962, 95, p. 174 and Bioorganic and Med. Chem. Lett. 10, 2000, p. 2311, which can be applied by analogy. For this purpose, the iodide salt is preferably used in at least an equimolar amount, based on the tri($C_1$-$C_6$-alkyl)silyl chloride, particularly in excess, based on the tri($C_1$-$C_6$-alkyl)silyl chloride. In this case, the preferred procedure is such that the tri($C_1$-$C_6$-alkyl)silyl iodide, particularly trimethylsilyl iodide, is initially prepared by treatment of the corresponding tri($C_1$-$C_6$-alkyl)silyl chloride with an iodide salt, particularly an alkali metal iodide, such as lithium iodide, potassium iodide or sodium iodide and the reaction product is added to the compound of the general formula (I). The preparation is preferably carried out in a suitable solvent, particularly in an aprotic solvent, such as acetonitrile or propionitrile.

In situ preparation of tri($C_1$-$C_6$-alkyl)silyl iodide can be achieved by reacting the corresponding hexa($C_1$-$C_6$-alkyl) disilane, especially hexamethyldisilane (HMDS) with iodine. Suitable methods for this are known, e.g. from Synthesis Commun. 1974, p. 740; Chem. Commun. 2003, p. 1266; Carb. Lett. 1998, 3, p. 179, which can be applied by analogy.

For this purpose, the hexa-($C_1$-$C_6$-alkyl)disilan, especially HMDS, is preferably reacted with elemental iodine in a first step, followed by addition of the compound of formula (I) to the thus obtained reaction mixture. The reaction of hexa-($C_1$-$C_6$-alkyl)disilan, especially HMDS, with iodine can be performed in bulk or in an inerte organic solvent. Suitable inert solvents include, in particular, halogenated hydrocarbons, such as trichloromethane and dichloromethane. The reaction of hexa-($C_1$-$C_6$-alkyl)disilan, especially HMDS, with elemental iodine is frequently performed at temperatures in the range of 0 to 110° C., in particular, in the range of 0 to 60° C. Alternatively, hexa-($C_1$-$C_6$-alkyl)disilan, especially HMDS, can be reacted with iodine and the compound of formula (I). This alternative is preferably performed in an inert solvent. Suitable inert solvents include, in particular, halogenated hydrocarbons such as trichloromethane and dichloromethane. Preferably, hexa-($C_1$-$C_6$-alkyl)disilan and iodine are reacted in a molar ratio in the range of 0.5:1 to 1:0.5, in particular in a molar ratio of about 1:1. Preferably, hexa-($C_1$-$C_6$-alkyl)disilan and the compound of formula (I) are used in a molar ratio in the range of 0.5:1 to 1:1, in particular, in a molar ratio in the range of 0.5:1 to 0.8:1. Preferably, iodine and the compound of formula (I) are employed in a molar ratio in the range of 0.5:1 to 1:1, in particular, in a molar ratio in the range of 0.5:1 to 0.8:1.

The compound of the formula (I) is generally reacted with the tri($C_1$-$C_6$-alkyl)silyl iodide in an inert organic solvent or diluent. Preference is given to aprotic solvents, particularly those having a low content of protic impurities such as water, alcohols or acid. The content of protic impurities in the solvent is preferably less than 1000 ppm. Preferably before use in the method according to the invention, the aprotic solvent is treated to reduce the content of protic impurities, particularly water, by treatment with suitable absorbents, for example, with molecular sieves of pore size 3 to 4 Angström. Preferred organic solvents are alkenes and cycloalkenes, such as isobutene, amylenes (1-pentene, 2-pentene, 2-methylbut-1-ene, 3-methylbut-1-ene and mixtures thereof), cyclopentene and cyclohexene, haloalkanes, such as dichloromethane, trichloromethane, dichloroethane, aromatic hydrocarbons such as toluene and xylenes, and also alkyl nitriles such as acetonitrile, and also mixtures of the abovementioned solvents. The solvent is preferably selected such that all constituents are present in dissolved form. The total concentration of compound of the formula (I) is preferably in the range of 5 to 70% by weight, particularly 10 to 50% by weight, based on the total weight of all reagents and solvents. For example, the method of the invention can be performed in an aprotic solvent, which is different from alkenes and which optionally contains from 5 to 100 mol-%, based on the compound (I), of an alkene or cycloalkene as a stabilizing additive. It is also possible to perform the reaction in at least one alkene as a solvent. It is also possible to add an alkene as a stabilizer for scavenging HI or $I_2$, after having performed the reaction.

The compound of the formula (I) is preferably reacted with the tri($C_1$-$C_6$-alkyl)silyl iodide at temperatures in the range of −20 to 110° C., particularly in the range of 0 to 80° C. and especially in the range of 20 to 65° C. The reaction may be carried out at ambient pressure, at reduced or elevated pressure. The reaction is typically conducted at a pressure in the range of 900 to 1100 mbar.

The reaction product resulting from the reaction of the compound of the formula (I) with the tri($C_1$-$C_6$-alkyl)silyl iodide is preferably not isolated, but is reacted without further isolation or purification with the compound of the formula (II), particularly in the presence of the base, wherein the compound of the formula (II) is obtained. The reaction product resulting from the reaction of the compound of the formula (I) with the tri($C_1$-$C_6$-alkyl)silyl iodide can also be purified or isolated, for example by removing volatile constituents from the reaction mixture, preferably under reduced pressure and/or by co-evaporation with suitable low-boilers, e.g. alkanes such as hexane, cyclohexane or heptane, or aromatic compounds such as toluene.

Optionally, an inorganic base can be added to the reaction product obtained in step a.1) prior to the reaction with the compound of formula (II) in step a.2). Frequently, the inorganic base is selected from alkali carbonates, alkali bicarbonates, alkaline earth carbonates and alkaline earth bicarbonates, in particular from alkali carbonates, such as lithium, sodium and potassium carbonate, and alkali bicarbonates such as sodium- or potassium bicarbonate. If desired, this inorganic base is preferably added in an amount of 0.01 to 0.5 equivalents per mol of the compound of formula (I), i.e. in case of a carbonate in an amount of 0.005 mol to 0.25 mol per mol of the compound of formula (I) and in case of a bicarbonate in an amount of 0.01 mol to 0.5 mol per mol of the compound of formula (I).

The reaction product obtained in step a.1, i.e. from the treatment of the compound (I) with the tri($C_1$-$C_6$-alkyl)silyl iodide, is reacted in accordance with the invention in step a.2 with the compound of the formula (II).

The reaction in step a.2 takes place in the presence of at least one base. In order to avoid secondary reactions, the base is preferably used in at least an equimolar amount, based on the compound of the formula (I). In particular, the base is used in an amount of 1 to 3 mol per mole of the compound of the formula (I), particularly in an amount of 1 to 1.5 mol per mole of the compound of the formula (I).

Preferred bases are primarily amine bases, particularly tertiary amines, especially pyridine bases and also tertiary aliphatic or cycloaliphatic amines. Suitable pyridine bases are, for example, pyridine, quinoline and $C_1$-$C_6$-alkyl-substituted pyridines, particularly mono-, di- and tri($C_1$-$C_6$-alkyl)pyridines such as 2,6-di($C_1$-$C_6$alkyl)pyridines, e.g. 2,6-dimethylpyridine or 2,6-bis(tert-butyl)pyridine, and collidine. Suitable tertiary aliphatic or cycloaliphatic amines are tri($C_1$-$C_6$-alkyl)amines such as trimethylamine, triethylamine, diisopropylmethylamine, tri-n-butylamine or isopropyldimethylamine, $C_3$-$C_8$-cycloalkyl-di($C_1$-$C_6$-alkyl)amines such as cyclohexyldimethylamine, N—($C_1$-$C_6$-alkyl)piperidine such as N-methylpiperidine, and di($C_3$-$C_8$-cycloalkyl)-$C_1$-$C_6$-alkylamines such as biscyclohexylmethylamine. Particular preference is given to tri($C_1$-$C_8$-alkyl)amines, especially trimethylamine and triethylamine. Suitable bases are also inorganic bases, selected from the group consisting of alkali carbonates, alkali bicarbonates, alkaline earth carbonates and alkaline earth bicarbonates, in particular from alkali carbonates, such as lithium, sodium and potassium carbonate, and alkali bicarbonates such as sodium- or potassium bicarbonate.

Preferably, the base used in step a.2 comprises at least one amine base, in particular at least one tertiary amine. In particular, the base comprises a combination of at least one amine base, in particular at least one tertiary amine, and at least one inorganic base, selected from the group consisting of alkali carbonates, alkali bicarbonates, alkaline earth carbonates and alkaline earth bicarbonates, in particular from alkali carbonates and alkali bicarbonates. If a combination of amine base and inorganic base is used, the amine base is preferably employed in an amount of 1 to 2 mol per mol of the compound of formula (I), in particular in an amount of 1 to 1.5 mol per mol of the compound of formula (I). In this combination, the inorganic base is preferably employed in an amount of 0.01 to 0.5 equivalents per mol of the compound of formula (I), i.e. in case of a carbonate in an amount of 0.005 mol to 0.25 mol per mol of the compound of formula (I) and in case of a bicarbonate in an amount of 0.01 mol to 0.5 mol per mol of the compound of formula (I).

The compound of the formula (II) is generally used in such an amount that the molar ratio of compound of the formula (I) to the compound of the formula (II) is in the range of 1:3 to 3:1, particularly in the range of 1:2 to 2:1, particularly preferably in the range of 1:1.5 to 1.5:1, and especially in the range of 1:1.1 to 1.1:1.

Preferably, step a.2) is performed in the presence of at least one further reagent, which is selected from elemental iodine, iodide salts, triarylphosphine oxides and mixtures thereof. Suitable iodine salts include alkalimetall iodides and also tetraalkylammonium iodides, in particular tetra-$C_1$-$C_6$-alkylammonium iodides, such as tetraethylammonium iodide and tetrapropylammonium iodide and especially tetrabutylammonium iodide. Preference is given to alkalimetal iodides, in particular to NaI and KI. A suitable triarylphosphineoxide is triphenylphosphineoxide. In particular, step a.2) is performed in the presence of at least one further reagent, which is selected from the group consisting of elemental iodine and iodide salts, especially from the group consisting of elemental iodine and alkalimetal iodides and mixtures thereof. Especially, step a.2) is performed in the presence of a mixture of elemental iodine and iodide salts, in particular in the presence of a mixture of elemental iodine and alkalimetal iodide salts and very especially in the presence of a mixture of elemental iodine and KI or in the presence of a mixture of elemental iodine and NaI.

In a first preferred embodiment A of the invention, the reaction in step a.2 takes place in the presence of iodine. In this embodiment, the tri($C_1$-$C_6$-alkyl)silyl iodide is preferably used in an amount of 0.9 to 1.1 mol, especially in an amount of 0.9 to 1 mol, per mole of the compound of the formula (I), and iodine is preferably used in an amount of 0.005 to 0.5 mol, especially 0.005 to 0.1 mol per mole of the compound of the formula (I).

In a further preferred embodiment B of the invention, the reaction in step a.2 takes place in the presence of an iodide salt. In this embodiment, the tri($C_1$-$C_6$-alkyl)silyl iodide is preferably used in an amount of 0.9 to 1.1 mol, especially in an amount of 0.9 to 1 mol, per mole of the compound of the formula (I), and the iodine salt is preferably used in an amount of 0.005 to 0.5 mol, especially 0.005 to 0.1 mol per mole of the compound of the formula (I). Suitable iodide salts, in addition to alkali metal iodides, are primarily tetraalkylammonium iodides, particularly tetra-$C_1$-$C_6$-alkylammonium iodide, such as tetraethylammonium iodide, tetrapropylammonium iodide and especially tetrabutylammonium iodide. Particular preference is given to alkalimetal iodides, in particular to NaI and KI.

In a further preferred embodiment C of the invention, the reaction in step a.2 takes place in the presence of a mixture of elemental iodine and an iodide salt. In this embodiment, the tri($C_1$-$C_6$-alkyl)silyl iodide is preferably used in an amount of 0.9 to 1.1 mol, especially in an amount of 0.9 to 1 mol, per mole of the compound of the formula (I), the elemental iodine is preferably used in an amount of 0.005 to 0.5 mol, especially 0.005 to 0.1 mol per mole of the compound of the formula (I) and the iodine salt is preferably used in an amount of 0.005 to 0.5 mol, especially 0.005 to 0.1 mol per mole of the compound of the formula (I). Suitable iodide salts, in addition to alkali metal iodides, are primarily tetraalkylammonium iodides, particularly tetra-$C_1$-$C_6$-alkylammonium iodide, such as tetraethylammonium iodide, tetrapropylammonium iodide and especially tetrabutylammonium iodide. Particular preference is given to alkalimetal iodides, in particular to NaI and KI.

In a further preferred embodiment D of the invention, the reaction in step a.2 takes place in the presence of a triarylphosphine oxide. In this embodiment, the tri($C_1$-$C_6$-alkyl)silyl iodide is preferably used in an amount of 0.9 to 1.1 mol, especially in an amount of 0.9 to 1 mol, per mole of the compound of the formula (I), and the triarylphosphine oxide is preferably used in an amount of 0.005 to 0.5 mol, especially 0.005 to 0.1 mol per mole of the compound of the formula (I). A suitable triarylphosphine oxide is particularly triphenylphosphine oxide.

In an equally preferred embodiment of the invention, none of the abovementioned further reagents is added in step a.2).

In a very preferred embodiment the following course of action is taken. First, hexa-($C_1$-$C_6$-alkyl)disilan, in particular HMDS, is reacted with iodine followed by reacting the obtained reaction mixture with the compound of the formula (I). Usually, this reaction is performed under the conditions mentioned above, in particular under the above mentioned preferred conditions. Then, an inorganic base, which is in particular selected from alkali carbonates, alkalimetal bicarbonates and mixtures thereof, is added to the thus obtained reaction mixture and the thus obtained mixture is subsequently reacted with the compound of the formula (II) in the presence of an amine base. With regard to the reaction conditions, amount of base and reagents the above mention applies similarly. According to this embodiment, step a.2) is preferably performed in the presence of a reagent, which is selected from the group consisting of elemental iodine and iodine salts, in particular from elemental iodine and alkalimetal iodides and mixtures thereof. According to this embodiment, step a.2) is especially performed in the presence of a mixture of elemental iodine and iodine salts, in particular in the presence of a mixture elemental iodine and alkalimetal iodides and especially in the presence of a mixture of elemental iodine and KI or in the presence of a mixture of elemental iodine and NaI. With regard to the relative amounts of these reagents the statements with regard to embodiments A, B and D apply analogously, Step a.2), i.e. the reaction of the reaction product resulting from treatment of the compound of the formula (I) with the tri($C_1$-$C_6$-alkyl)silyl iodide, with the compound of the formula (II), is generally carried out in one of the abovementioned inert organic solvents or diluents. Preference is also given here to the abovementioned aprotic solvents, particularly those having a low content of protic impurities such as water, alcohols or acid. The content of protic impurities in the solvent is preferably less than 1000 ppm. Preferably before use in the method according to the invention, the aprotic solvent is treated to reduce the content of protic impurities, particularly water, by treatment with suitable absorbents, for example, with molecular sieves of pore size 3 to 4 Angström. Preferred organic solvents are haloalkanes, such as dichloromethane, trichloromethane, dichloroethane, aromatic hydrocarbons such as toluene and xylenes, dimethylamides of aliphatic carboxylic acids such as dimethylformamide (DMF) and dimethylacetamide, and also alkyl nitriles such as acetonitrile, and also mixtures of the abovementioned solvents. The solvent is preferably selected such that all constituents are present in dissolved form. The total concentration of compound of the formula (I) and (II) is preferably in the range of 5 to 75% by weight, particularly 10 to 65% by weight, or 15 to 60% by weight, based on the total weight of all reagents and solvents.

The reaction in step a.2) is preferably carried out at temperatures in the range of −20 to 110° C., particularly in the range of 0 to 80° C. The reaction may be carried out at ambient pressure, at reduced or elevated pressure. The reaction is typically conducted at a pressure in the range of 900 to 1100 mbar.

The compound of the formula (III) obtained by the reaction in step a) may be isolated by customary work-up methods and optionally be purified by crystallization and/or chromatography. Alternatively, it is possible to directly subject the compound of the formula (III) obtained by the reaction in step a) to at least partial or complete deprotection so as thus to obtain the compounds of the formulae (IIIa) where $R^4$=H, (IIIc) where $R^4$=H or the compound of the formula (IIIb) or (IV).

The deprotection of the compound of the formula (III) is achieved in analogy to known deprotecting reactions and is preferably carried out by hydrolysis methods. The conditions for cleavage of these protecting groups are familiar to those skilled in the art, e.g. from P. G. M Wuts et al., "Greene's Protecting Groups in Organic Synthesis, 4th Edition, Wiley 2006 and the literature cited therein, or the references cited at the outset for the preparation of 2'-O-fucosyllactose.

According to a first embodiment b.1) of the invention, the compound of the formula (III) is treated with water in the presence of an acid. In this manner, a complete cleavage of all protecting groups from the compound of the formula (III) is generally achieved and the 2'-O-fucosyllactose is obtained.

Suitable acids are mineral acids, such as hydrochloric acid, sulfuric acid, phosphoric acid, acidic salts of mineral acids such as alkali metal hydrogen phosphates and dihydrogen phosphates or alkali metal hydrogen sulfates, e.g. sodium dihydrogen phosphate or potassium hydrogen phosphate, in addition organic carboxylic acids, such as acetic acid, propionic acid, dichloroacetic acid, trichloroacetic acid or trifluoroacetic acid, and organic sulfonic acids, such as methanesulfonic acid. The acids are typically used as dilute aqueous acids, e.g. as 5 to 70% strength by weight solutions. Frequently, the dilute aqueous acid is used in combination with a suitable organic solvent. Examples thereof are organic solvents miscible with water, such as $C_1$-$C_4$-alkanols, e.g. methanol, ethanol, isopropanol, 1-butanol or tert-butanol, cyclic ethers such as tetrahydrofuran or dioxane, and also organic solvents having only limited miscibility with water, e.g. haloalkanes such as dichloromethane, trichloromethane, dichloroethane, aromatic hydrocarbons such as toluene and xylenes, and also dialkyl ethers such as diethyl ether, diisopropyl ether or methyl tert-butyl ether. The reaction conditions required are known to a person skilled in the art, e.g. from P. G. M. Wuts et al., loc. cit. and the literature cited therein, or the references cited at the outset for the preparation of 2'-O-fucosyllactose. Subsequent to the removal of the protecting groups, the acid is usually neutralized and then the product is isolated by removal of water. Neutralization can be achieved by using a base, which is conventionally used for this purpose, including alkalimetal hydroxides, alkalimetal carbonates and alkalimetal bicarbonates. Neutralization can also be achieved by using a basic or strongly basic ion-exchange resin, because this will allow for neutralization without formation of salts in the solution of the product.

In the embodiment b.1), cleavage of the protecting groups can also be achieved by means of an acidic ion-exchange resin in aqueous media. Thereby, a separate neutralization step can be avoided.

According to a further embodiment b.2) of the invention, the compound of the formula (III), in which $R^1$ is an $SiR^{12}R^{13}R^{14}$ residue, is firstly treated with a desilylating reagent, wherein a compound of the formula (IIIb') is obtained:

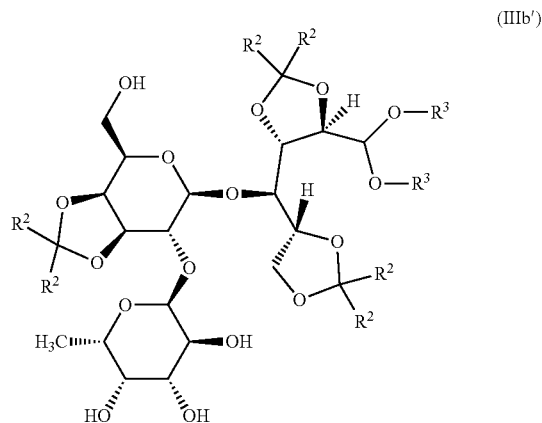

(IIIb')

The compound of the formula (III), in which $R^1$ is an $SiR^{12}R^{13}R^{14}$ residue, corresponds to the compound of the formula (IIIa), where $R^{1a}$ is an $SiR^{12}R^{13}R^{14}$ residue and $R^4$ is an $SiR^aR^bR^c$ residue. The compound of the formula (IIIb') corresponds to the compound of the formula (IIIb), where $R^4$ is hydrogen.

The desilylation may be carried out in one step such that both the $SiR^{12}R^{13}R^{14}$ group and the $SiR^aR^bR^c$ groups are simultaneously cleaved off. It can also be carried out successively if the $SiR^{12}R^{13}R^{14}$ and $SiR^aR^bR^c$ groups have different reactivities.

Suitable reagents for the desilylation are, for example, the abovementioned $C_1$-$C_4$ alcohols, particularly methanol, with or without addition of water, and also alkali metal or alkaline earth metal carbonates and hydrogen carbonates, such as lithium carbonate, sodium carbonate, potassium carbonate, sodium hydrogen carbonate and potassium hydrogen carbonate, preferably in solution in one of the abovementioned $C_1$-$C_4$ alcohols, particularly methanol, with or without addition of water. Suitable desilylating reagents are also tetraalkylammonium fluorides, which are preferably used in polar, aprotic organic solvents, e.g. cyclic ethers such as tetrahydrofuran or dioxane, or in di-$C_1$-$C_4$-alkylamides of aliphatic carboxylic acids such as dimethylformamide or dimethylacetamide, or alkyl nitriles such as acetonitrile or mixtures of the abovementioned polar, aprotic organic solvents. The reaction conditions required are known to a person skilled in the art, e.g. from P. G. M. Wuts et al., loc. cit. and the literature cited therein.

Subsequently, the remaining protecting groups are removed by treating the compound of the formula (IIIb') with water in the presence of an acid. This can be effected in the manner described for embodiment b1).

According to a further embodiment b.3) of the invention, the compound of the formula (III), in which $R^1$ is a $C(O)R^{11}$ residue, is firstly treated with a desilylating reagent, wherein a compound of the formula (IIIc') is obtained:

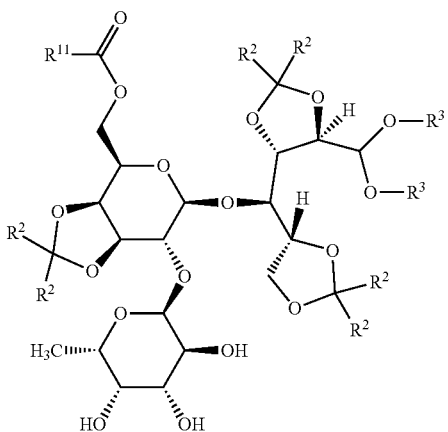
(IIIc')

The compound of the formula (IIIc') corresponds to the compound of the formula (IIIc), where $R^4$ is hydrogen. Subsequently, the C(O)—$R^{11}$ group and the remaining protecting groups are simultaneously or successively removed.

The desilylation of the compound of the formula (III), in which $R^1$ is a C(O)$R^{11}$ residue, is achieved in analogy to embodiment b2) by treatment of the compound (III) with a desilylating reagent. The reaction conditions required for the desilylation are known to a person skilled in the art, e.g. from P. G. M. Wuts et al., loc. cit. and the literature cited therein.

The subsequent cleavage of the ester group C(=O)—$R^{11}$ is achieved in a manner known per se by basic saponification or by base-catalyzed or enzyme-catalyzed transesterification. Methods for this purpose are known, e.g. from P. G. M. Wuts et al. loc. cit. or from Kociensky et al. Protective groups, 3rd Edition, Chapter 4.6, Thieme 2005. The remaining C($R^2$)$_2$ and O$R^3$ protecting groups are then removed in a manner known per se, e.g. by treatment with an aqueous acid, as already described in connection with embodiment b1).

According to a further embodiment b.4) the procedure can, alternatively, also be such that the C($R^2$)$_2$ and O$R^3$ protecting groups are initially removed from the compounds of the formula (IIIc'), e.g. by treatment with an aqueous acid, as already described in connection with embodiment b1), wherein the compound of the general formula (IV) is obtained as previously described. The ester group C(=O)—$R^{11}$ can then be cleaved from the compound of the formula (IV) in a manner known per se. e.g. by basic saponification or basic transesterification or by enzyme-catalyzed transesterification.

Alternatively, the procedure can also be such that the C($R^2$)$_2$ and O$R^3$ protecting groups are initially removed from the compound of the formula (IIIc'), e.g. by treatment with an aqueous acid, as already described in connection with embodiment b1), and then the ester group C(=O)—$R^{11}$ is then cleaved in a manner known per se by basic saponification or by enzyme-catalyzed transesterification.

According to a particularly preferred embodiment b.5), the compound of formula (III) is treated with a $C_1$-$C_4$-alkanol and an alkalimetal base first, whereby a compound of formula (IIIb') is obtained, followed by removal of the remaining protective groups under acidic conditions. In this embodiment, $R^{11}$ is preferably $C_1$-$C_4$-alkyl such as methyl, ethyl or tert-butyl. Thereby, the desilylation and removal of the ester group C(=O)—$R^{11}$ can be linked to each other and may be cleaved in a single step. Suitable reagents here are in turn the abovementioned alkali metal hydroxides and carbonates in $C_1$-$C_4$-alkanols, such as methanol as solvent. For this purpose, the combination of methanol with sodium carbonate or potassium carbonate is particularly useful. The reaction conditions required for this purpose are familiar to those skilled in the art and may be determined by routine experiments. Preferably, simultaneous desilylation and removal of the ester group C(=O)—$R^{11}$ can be achieved by treatment of (III) with the alkalimetal base in a $C_1$-$C_4$-alkanol, such as methanol, at temperatures in the range of 20 to 50° C. The amount of alkalimetal base, in particular alkalimetal carbonate is preferably 3 to 10 equivalents and especially 4 to 7 equivalents, based on the compound (III), i.e. in case of the alkalimetal carbonate 1.5 to 5 mol, in particular 2 to 3.5 mol per mole of compound (III). The cleavage of the protective groups C($R^2$)$_2$ and O$R^3$ can be achieved by analogy to the methods described under b.1).

The 2'-O-fucosyllactose obtained after removal of the protective groups can be purified by using conventional purification methods such as chromatography or crystallization, optionally with the aid additives, such as charcoal, silica or polyvinyl pyrrolidone. Typical conditions for the crystallization of 2'-O-fucosyllactose can be found in Chem. Ber. 1956, 11, 2513. Depending on the reaction conditions and the method of purification the obtained 2'-O-fucosyllactose may contain lactose, z.B. in an amount of 1% to 20%, based on the weight of the product. Chemical purity of 2'-O-fucosyllactose, minus lactose, is usually at least 90%, in particular at least 95% or higher. However, lactose is not a problematic impurity, because the amount of lactose is not problematic for the use of 2'-O-fucosyllactose in food.

In particular, the method of the invention allows for producing 2'-O-fucosyllactose in a manner, such that, even before work-up, the amount of the undesirable ß-isomer ß-2'-O-fucosyllactose (=ß-L-fucopyranosyl)-(1→2)-O-ß-D-galactopyranosyl-(1→4)-D-glucopyranose) is as low that purification of the reaction product yields 2'-O-fucosyllactose, which contains less than 1% by weight, in particular less than 0.5% by weight ß-2'-O-fucosyllactose, based on the total amount of 2'-O-fucosyllactose. This was not possible so far. Contrary to the methods of prior art, the method of the invention does not require transition metal catalysts for hydrogenolytic cleavage of benzyl protective groups and, thus, the concentration of transition metals in the 2'-O-fucosyllactose obtainable by the method of the invention is frequently less than 1 ppm and in particular below the level of detection.

The compound of the formula (I) used in step a) of the method according to the invention is known, e.g. from Synlett. 1996, 499; Org. Lett. 13(3) (2001) 2081-2084; and Tetrahedron Asym., 16 (1) (2005) 149-158.

Compounds of the formula (II), where $R^1$ is a C(=O)—$R^{11}$ residue, are known, e.g. from the references cited at the outset, or from Tetrahedron Letters, 1981, 22 (50), 5007-5010, WO 2010/115934, WO 2010/115935 and Carbohydrate Research, 1981, 88, 51-60, or may be prepared in analogy to the methods described therein.

Compounds of the formula (II), where $R^1$ is an $SiR^{12}R^{13}R^{14}$ residue, correspond to the compounds of the formula (IIa). Said compounds are novel, provided that the radical $R^1$ is not a radical $SiR^{12}R^{13}R^{14}$, wherein $R^{12}$ and $R^{13}$ are methyl and $R^{14}$ is tert-butyl, and wherein $R^2$ and $R^3$ are methyl (see H. Kogelberg et al. Carbohydrate Research 201 (1990), 161-173). Therefore, compounds of the formula (IIa) likewise form part of the subject matter of the present invention, provided that the radical $R^1$ is not tert-butyldimethylsilyl, if $R^2$ and $R^3$ are methyl.

The compounds of the formula (IIa) may be prepared in a simple manner from the compounds of the formula (IIb) by selective silylation of the $CH_2$—OH group.

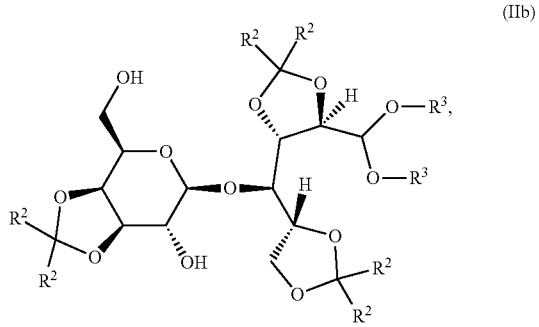

$R^2$ and $R^3$ in formula (IIb) are as defined above, particularly as defined below:
$R^2$ is in particular $C_1$-$C_4$-alkyl and especially methyl, or two $R^2$ residues attached to the same carbon atom are together 1,5-pentanediyl and thus form a cyclohexane-1,1-diyl residue with the carbon atom to which they are attached. All $R^2$ residues are especially methyl.
$R^3$ is particularly $C_1$-$C_4$-alkyl and especially methyl.

For the selective silylation, the compound of the formula (IIb) is typically reacted with a suitable silylating reagent, e.g. a compound of the formula $SiXR^{12}R^{13}R^{14}$, where $R^{12}$, $R^{13}$ and $R^{14}$ are as defined previously and are especially methyl and X is halogen, particularly chlorine. The reaction with the silylating reagent is preferably carried out in the presence of a base.

For the selective silylation, 0.9 to 2 mol, particularly 1 to 1.5 mol, especially about 1.1 mol of the silylating reagent is typically used per mole of the compound of the formula (IIb).

In order for the reaction to proceed selectively, the reaction of (IIb) is preferably carried out in the temperature range from −40 to +40° C., particularly in the range from −20 to +20° C., especially preferably in the range from −5 to +5° C., e.g. at about 0° C.

Suitable bases are primarily amine bases, particularly secondary and tertiary amines, especially pyridine bases and tertiary aliphatic or cycloaliphatic amines. Suitable pyridine bases are, for example, pyridine, quinoline and $C_1$-$C_6$-alkyl-substituted pyridines, particularly mono-, di- and tri($C_1$-$C_6$-alkyl)pyridines such as 2,6-di($C_1$-$C_6$-alkyl)pyridines and collidine. Suitable tertiary aliphatic or cycloaliphatic amines are tri($C_1$-$C_6$-alkyl)amines such as triethylamine, diisopropylmethylamine, tri-n-butylamine or isopropyldimethylamine, $C_3$-$C_8$-cycloalkyl-di($C_1$-$C_6$-alkyl)amines such as cyclohexyldimethylamine, N—($C_1$-$C_6$-alkyl)piperidine such as N-methylpiperidine and di($C_3$-$C_8$-cycloalkyl)-$C_1$-$C_6$-alkylamines such as biscyclohexylmethylamine.

The base is typically used in an amount of 0.9 to 2 mol, particularly in an amount of 1 to 1.5 mol per mole of the compound of the formula (IIb).

The compound of the formula (IIb) is reacted with the silylating reagent, generally in an inert organic solvent or diluent. Preference is given to aprotic solvents, particularly those having a low content of protic impurities such as water, alcohols or acid. Preferred organic solvents are haloalkanes, such as dichloromethane, trichloromethane, dichloroethane, aromatic hydrocarbons such as toluene and xylenes, dialkyl ethers such as diethyl ether, diisopropyl ether, methyl tert-butyl ether, cyclic ethers such as tetrahydrofuran or dioxane, dialkylamides of aliphatic carboxylic acids such as dimethylformamide or dimethylacetamide and also alkyl nitriles such as acetonitrile, and also mixtures of the abovementioned solvents. The solvent is preferably selected such that all constituents are present in dissolved form. The total concentration of compound of the formulae (I) and (II) is preferably in the range of 5 to 50% by weight, particularly 10 to 40% by weight, based on the total weight of all reagents.

The compound of the formula (IIIa) can be worked-up by filtration, by extraction or in some cases by distillation.

The compounds of the formula (IIb) are known, e.g. from Carbohydrate Research, 212 (1991), pp. C1-C3; Tetrahedron Lett., 31 (1990) 4325; Carbohydrate Research, 75 (1979) C11; Carbohydrate Research, 88 (1981) 51; Chem. 5 (1999) 1512; WO 2010/070616, WO 2012/113404, WO 2010/115934 and WO 2010/115935 or may be prepared by the methods described therein.

As already mentioned, the 2'-O-fucosyllactose obtainable by the method according to the invention, in comparison to the known 2'-O-fucosyllactose, is characterized in that it does not comprise, or only comprises in much lower fractions, those impurities which cannot be removed. In particular, the 2'-O-fucosyllactose obtainable by the method according to the invention does not comprise significant amounts of impurities, particularly no impurities resulting from hydrogenation, which would be of concern for use in foodstuffs.

Accordingly, such a 2'-O-fucosyllactose is suitable itself as foodstuff and also as additive for foodstuff. Examples of foodstuff in which the 2'-O-fucosyllactose may be used are familiar to those skilled in the art, e.g. from the prior art cited at the outset. Here, this can take the form of compositions based on naturally occurring products, e.g. dairy products, and also artificially prepared formulations, for example, for dietary or medicinal nutrition. The latter can be ready-to-use formulations and can be used directly, or may take the form of concentrated formulations, e.g. liquid or semi-solid concentrates, or solid products such as granules, flakes or powder which are converted into a ready-to-use formulation before use by addition of liquid, particularly water, or which are incorporated into a conventional foodstuff.

The concentrates and also the ready-to-use formulations can be solid, liquid or semi-solid formulations.

In particular, the foodstuffs, in which the 2'-O-fucosyllactose according to the invention is used, are foodstuff compositions for child nutrition, particularly in baby formula and especially infant formula.

In general, the foodstuffs, in which the 2'-O-fucosyllactose according to the invention is used, are solid, semi-solid or liquid foodstuff compositions, particularly semi-solid or especially liquid foodstuff compositions.

The foodstuff compositions, i.e. the ready-to-use foodstuff compositions and the concentrates, may be prepared in a manner known per se by incorporating the 2'-O-fucosyllactose obtainable according to the invention into a foodstuff formulation. This foodstuff formulation may comprise other nutrients, in addition to the 2'-O-fucosyllactose, and generally comprises at least one carrier suitable for foodstuff, wherein the latter may be solid, liquid or semi-solid. The carrier can be a foodstuff or a substance with nutritional value, or it may be a substance which itself has no nutritional value, e.g. dietary fiber or water.

The examples which follow serve to illustrate the invention.

The following abbreviations were used:
d: doublet
s: singlet
t: triplet
m: multiplet
mc.: centered multiplet
CHE: Cyclohexane
DCM: Dichloromethane, preferably stabilized with amylene or without any stabilizer
DMF: Dimethylformamide
of th.: of theory
EE: Ethyl acetate
EtOH: Ethanol
eq: Molar equivalents
b.p. Boiling point
MeOH: Methanol
$NEt_3$: Triethylamine
RT: Ambient temperature, about 22° C.
Rt.: Retention time
TMS: Trimethylsilyl
TMSCl: Trimethylsilyl chloride
TMSI: Trimethylsilyl iodide
2'-Fl: 2'-O-fucosyllactose If not stated to the contrary, 2'-O-fucosyllactose (2'-FL) refers to the alpha anomer.

If not indicated otherwise, the HPLC analysis was performed using an Agilent Series 1200 and a Luna-NH2 column (3 μm; 250×4.6 mm, 100 Å). The column was maintained at 35° C. and operated at 135 bar.

Acetonitrile/water 75/25 v/v was used as eluent; detection was with an RID detector. The flow rate was 1 mL/min, the run time 10 min. The sample volume was 5 μL.

For the sample preparation, 10 mg of sample were in each case dissolved in 1 mL of acetonitrile/water in a 75/25 ratio by volume.

In addition, the following High Performance Liquid Chromatography (HPLC) methods were used, where indicated below.

HPLC Method 2

HPLC analysis was performed using an Agilent Series 1200 and a Luna-NH2 column (3 μm; 250×4.6 mm, 100 Å). The column was maintained at 35° C. and operated at 204 bar.

Acetonitrile/water 82.5/17.5 v/v was used as eluent; detection was with an RID detector. The flow rate was 1 mL/min, the run time 10 to 40 min. The sample volume was 5 μL.

For the sample preparation, 100 mg of sample were in each case dissolved in 10 mL of acetonitrile/water in a 50/50 ratio by volume.

HPLC Method 3

HPLC analysis was performed using an Agilent Series 1200 and a Waters Spherisorb-NH2 column (3 μm; 250×4.6 mm, 80 Å). The column was maintained at 35° C. and operated at 112 bar.

Acetonitrile/water 82.5/17.5 v/v was used as eluent; detection was with an RID detector. The flow rate was 1 mL/min, the run time 10 to 40 min. The sample volume was 5 μL.

For the sample preparation, 100 mg of sample were in each case dissolved in 10 mL of acetonitrile/water in a 50/50 ratio by volume.

The retention times of the individual compounds vary over time, the reasons for variation include column degradation and composition of the sample. Before measurement, reference samples of the starting materials in question, products in question and by-products in question were always measured to determine the actual retention time.

Determination of the α/ß-Ratio

Using HPLC method 3, the ß-isomer of 2'-O-fucosyllactose has a retention time Rt of 10.2 min, whereas the target (desired) α-isomer has a retention time Rt of 11.6 min. These values vary over time as a result of degradation of the column and composition of the sample. In any case, the ß-isomer elutes before the α-isomer. In any case, reference samples of both isomers were always measured in order to determine the actual retention time.

EXAMPLES

Preparation Example 1: Preparation of tetrakistrimethylsilylfucose 2.5 g (15.1 mmol) of fucose were charged in 75 mL of DCM (0.2M solution). To this were added 6.78 g (4.4 eq.) of triethylamine and the mixture was cooled to 0° C. 7.35 g (4.4 eq.) of chlorotrimethylsilane were then added slowly dropwise at 0° C. and the reaction mixture was stirred for 1 h at 00° C. The mixture was allowed to warm to RT and, after a further 16 h at RT, 75 mL of pentane were added, the mixture was briefly stirred and then added to 100 mL of ice-water. After phase separation, the aqueous phase was reextracted three times with pentane, and the combined organic phases were washed successively twice with water and three times with NaCl solution. The organic phase was dried with $Na_2SO_4$, filtered and concentrated to dryness under reduced pressure. Yield: 6.6 g (97% of th.)

$^1$H-NMR ($CD_2Cl_2$): δ 5.0 (d, 1H), 4.0 (mc, 1H), 3.8, (m, 2H), 1.05 (d, 3H), 0.2-0.1 (4 s, 36H)

Preparation Example 2: Preparation of tetrakistrimethylsilylfucose

In a manner analogous to preparation example 1, 34.9 g of the title compound are obtained by the method described above from 13 g of fucose in 386 mL of DMF with 38.2 g of TMSCl and 35.3 g of $NEt_3$.

Preparation Example 3: Preparation of 4-O-(3,4-isopropylidene-ß-D-galactopyranosyl)-2,3;5,6-bis-O-isopropylidene-D-glucose Dimethyl Acetal (Compound II-1: Compound of the Formula (II) where $R^1$=H, $R^2$=$CH_3$ and $R^3$=$CH_3$)

205.4 g (0.6 mol) of lactose were charged in 409 mL of 1,4-dioxane. To this were added 28.44 g (0.12 mol=0.2 eq.) of DL-camphorsulfonic acid and 376.4 mL (3 mol=5 eq.) of dimethoxypropane. The mixture was heated under reflux for 4 h. 10.04 mL of triethylamine were then added. After cooling, the mixture was concentrated under reduced pressure (2 mbar) and 50° C., during which two times 300 mL of toluene each time were added and codistilled. The residue that remained was taken up in 1000 mL of methanol/water 9:1 v/v and stirred at 60° C. for 1 h. After removing the methanol under reduced pressure, 600 mL of DCM were added and the resulting solution was washed twice with 5% aqueous $NaHCO_3$ solution. After removal of the solvent under reduced pressure, the residue was taken up in 50 mL of ethyl acetate and was crystallized at −10° C. with addition of 50 mL of cyclohexane and 160 mL of diisopropyl ether.

Filtration and washing of the crystals with 2×50 mL of cold diisopropyl ether affords 118.9 g of the title compound with a purity of 92%.

$^1$H-NMR (CD$_2$Cl$_2$): δ 4.5 (t, 1H), 4.4 (d, 1H), 4.4-4.3 (m, 2H), 4.2 (m, 1H), 4.1-3.8 (m, 7H), 3.6 (m, 1H), 3.5 (m, 1H), 3.4 (s, 6H), 3.3 (d, 1H), 2.9 (s, 1H), 1.5 (2 s, 6H), 1.4 (s, 6H), 1.3 (s, 6H).

Preparation Example 4: Preparation of 4-O-(6-O-acetyl-3,4-isopropylidene-ß-D-galactopyranosyl)-2,3;5,6-bis-O-isopropylidene-D-glucose Dimethyl Acetal (Compound II-2: Compound of the Formula (II) where $R^1$=Acetyl, $R^2$=CH$_3$ and $R^3$=CH$_3$)

58.8 g (92% strength=0.106 mol) of the compound II-1 from preparation example 3 were dissolved in 183 mL of DCM. The solution was treated with 25.12 mL (0.181 mol) of NEt$_3$ and cooled to −5° C. To this was added dropwise a solution of 60.9 g (0.16 mol) of acetyl chloride dissolved in 61 mL of DCM over a period of 70 min. and the resulting mixture was stirred at 0° C. for 20 h. For the work-up, the mixture was treated with 100 mL of ice-water, the phases were separated and the aqueous phase was extracted twice with 50 mL of DCM each time.

The combined organic phases were washed successively with 50 mL of 1N aqueous hydrochloric acid, 50 mL of 5% aqueous NaHCO$_3$ solution, dried over Na$_2$SO$_4$ and concentrated under reduced pressure (250 mbar) at 40° C.

The title compound II-2 was obtained in an amount of 65.1 g with a purity of 73%. The product was reacted further directly or was purified to 90% purity by chromatography or crystallization of the secondary components from cyclohexane.

$^1$H-NMR (CD$_2$Cl$_2$): δ 4.5-4.4 (m, 2H), 4.4 (m, 1H), 4.4-4.2 (m, 2H), 4.2-4.1 (m, 2H), 4.1-3.9 (m, 5H), 3.5 (m, 1H), 3.4 (2 s, 6H), 2.1 (s 3H), 1.5 (s 2 6H), 1.4 (2 s 6H), 1.3 s, 6H).

Preparation Example 5: Preparation of 4-O-(6-O-trimethylsilyl-3,4-isopropylidene-ß-D-galactopyranosyl)-2,3;5,6-bis-O-isopropylidene-D-glucose dimethyl acetal (Compound II-3: Compound of the Formula (II) where $R^1$=TMS, $R^2$=CH$_3$ and $R^3$=CH$_3$)

A solution of 5.98 g of compound II-1 from preparation example 3 (85% strength, 1 eq.) and 1.55 mL (1.5 eq.) of NEt$_3$ in 23 mL of DCM at 00° C. was treated with a solution of 1.2 g (1.1 eq.) of TMSCl in 6 mL of DCM, and the resulting mixture was stirred at 0° C. for 6 h. For the work-up, 26 mL of heptane and 50 mL of ice-water were added to the mixture and the organic phase was separated. After drying the organic phase with saturated aqueous NaCl solution and removal of the solvent under reduced pressure, 5.7 g of the compound II-3 remained as crude product which was pure enough for further reactions. Purification by chromatography on silica gel or by distillation may be achieved (b.p. 130-140° C. at 0.1 mbar). Chromatography on 500 mL of silica gel with ethyl acetate/cyclohexane 7/3 v/v afforded 1.97 g of the compound:

$^1$H NMR in CD$_2$Cl$_2$: δ 4.4-4.2 (m, 3H); 4.2 (m, 1H), 4.2-3.6 (m, 10H), 3.4 (m, 1H), 3.3 (2 s, 6H), 1.4 (2 s, 6H), 1.3-1.2 (3 s, 12H), 0.1 (s, 9H).

Preparation Example 6: Preparation of 4-O-(6-O-pivaloyl-3,4-isopropylidene-ß-D-galactopyranosyl)-2,3;5,6-bis-O-isopropylidene-D-glucose-dimethyl Acetal (Compound II-4: Compound of the Formula (II) where $R^1$=C(=O)C(CH$_3$)$_3$, $R^2$=CH$_3$, and $R^3$=CH$_3$)

150 g (280 mmol) of compound II-1 ($R^2$=$R^3$=CH$_3$) from preparation example 3 were charged in 190 mL of DCM. To this were added 57.19 g (565 mmol) of triethylamine. A solution of 49.56 g (411 mmol) of pivaloyl chloride in 35 mL of DCM was added over a period of 2 h, so that the temperature was not allowed to rise above 27° C. Then, the reaction mixture was heated to reflux for 21 h (internal temperature: 49° C.). After cooling, the suspension was poured onto 410 mL of ice water and the resulting mixture was stirred for 10 min.

The organic phase was separated and the aqueous phase was extracted once with 95 mL of DCM. The combined organic phases were successively washed with 95 mL of water, 95 mL of saturated NaCl solution, dried over 45 g of Na$_2$SO$_4$ and the solids were filtered off. The filtrate was evaporated by means of rotary evaporation (40° C., 5 mbar) to afford 188.65 g of a product comprising 79.2% by weight of the title compound (89.2% of th.).

$^{13}$C NMR (CD$_2$Cl$_2$, 500 MHz): δ(ppm) 178.24, 110.40, 110.30, 108.55, 105.65, 103.95, 79.36, 78.35, 78.12, 76.72, 75.62, 74.60, 73.60, 71.36, 64.99, 63.09, 56.51, 53.54, 38.98, 28.25, 27.35, 27.26, 27.26, 27.26, 26.68, 26.39, 25.82, 24.51.

Example 1: Preparation of the Compound of the Formula IIIc, where $R^{11}$=CH$_3$, $R^2$=CH$_3$, $R^3$=CH$_3$ and $R^4$=H To a solution of 0.8 g of tetrakistrimethylsilylfucose (compound of the formula (I) where $R^{Si}$=trimethylsilyl, 1 eq.) in 3 mL of DCM were added dropwise at RT 5.2 mL of a 5% strength by weight solution of trimethylsilyl iodide in DCM and the mixture was stirred at RT for 20 min.

The solution thus obtained was added dropwise at 0° C. to a solution of 0.973 g (1 eq.) of the fucose acceptor II-2 from preparation example 4 and 0.523 g of 2,6-di-tert-butylpyridine in 3 mL of DCM and the mixture was stirred at RT for 16 h. 18 mL of methanol were added to the reaction mixture thus obtained and the mixture was stirred for 30 min. The methanolic mixture was then added to 25 mL of saturated aqueous NaHCO$_3$ solution and the phases were separated. The aqueous phase was extracted once more with 20 mL of DCM and the combined organic phases were washed with 20 mL of saturated aqueous Na$_2$SO$_3$ solution.

The organic phase was chromatographed on silica gel (200 mL of silica gel, DCM/MeOH 92/8), wherein 0.57 g of the fucose acceptor II-2 was recovered and 0.13 g of the protected title compound of the formula IIIc, where $R^{11}$=CH$_3$, $R^2$=CH$_3$, $R^3$=CH$_3$ and $R^4$=H, was obtained.

$^{13}$C-NMR (CD$_2$Cl$_2$): δ 171.00, 110.44, 110.20, 108.99, 105.92, 101.66, 97.88, 80.25, 77.97, 77.40, 76.22, 75.69, 75.64, 75.51, 74.04, 71.24, 71.17, 69.20, 66.92, 66.03, 63.60, 56.12, 53.54, 27.87, 27.45, 27.12, 27.11, 26.37, 25.62, 21.03, 17.04, 0.72, 0.72, 0.72, 0.57, 0.57, 0.57, 0.20, 0.20, 0.20.

Example 2: Preparation of the Compound of the Formula IIIc, where $R^{11}$=CH$_3$, $R^2$=CH$_3$, $R^3$=CH$_3$ and $R^4$=Si(CH$_3$)$_3$ In a manner analogous to example 1, 1.0 g of tetrakistrimethylsilylfucose and 1.22 g of compound II-2 from preparation example 4 were reacted in acetonitrile as solvent. The work-up differed from example 1 in that methanol was not added. After chromatography of the reaction product on silica gel, 0.28 g of the title compound and 0.67 g of the fucose acceptor II-2 used were obtained.

$^{13}$C-NMR (CD$_2$Cl$_2$): δ 110.4, 110.2, 109.0 106.0, 101.7, 97.9, 80.3, 78.0, 77.4, 76.3, 75.7, 75.6, 75.5, 74.1, 71.3, 71.2, 69.2, 69.0, 66.1, 63.6, 56.2, 53.6, 27.9, 27.5, 27.1, 26.4, 25.7, 21.1, 17.1, 0.8, 0.6, 0.2.

Example 3: Preparation of the Compound of the Formula IIIc, where $R^{11}$=CH$_3$, $R^2$=CH$_3$, $R^3$=CH$_3$ and $R^4$=Si(CH$_3$)$_3$ In a manner analogous to example 1, 2.5 g (5.5 mmol) of tetrakistrimethylsilylfucose were firstly reacted with 1.1 g of trimethylsilyl iodide. The reaction product was treated with 0.75 g of NEt$_3$, 2.5 g of molecular sieve and 1.4 g of iodine and subsequently reacted with 8.4 g (0.015 mol) of the compound II-2 from preparation example 4 at 40° C. for 48 h. After filtration on silica gel with EE/CHE 1:1 v/v, 2.1 g of the title compound were obtained (yield 40% of theory).

Example 4: Preparation of the Compound of the Formula IIIc, where $R^{11}$=CH$_3$, $R^2$=CH$_3$, $R^3$=CH$_3$ and $R^4$=Si(CH$_3$)$_3$ In a manner analogous to example 3, 3.26 g (7.2 mmol) of tetrakistrimethylsilylfucose were firstly reacted with 1.44 g of trimethylsilyl iodide. After 20 min., the volatile constituents were removed under reduced pressure. The residue (iodide) was coevaporated with 10 mL of n-heptane each time. The residue was then taken up in 10 mL of DCM and reacted with 20.79 g (14.4 mmol) of a 38% strength solution of compound II-2 from preparation example 4 in DCM in the presence of 0.98 g of NEt$_3$, 3.3 g of molecular sieve and 2.66 g of tetrabutylammonium iodide. After filtration on silica gel with EE/CHE 1:1 v/v, 3.8 g of the title compound were obtained (yield 57% of theory).

Example 5: Preparation of the Compound of the Formula IIIc, where $R^{11}$=CH$_3$, $R^2$=CH$_3$, $R^3$=CH$_3$ and $R^4$=Si(CH$_3$)$_3$ In a manner analogous to example 3, 3.26 g (7.2 mmol) of tetrakistrimethylsilylfucose were firstly reacted with 1.44 g of trimethylsilyl iodide. After 20 min., the volatile constituents were removed under reduced pressure. The resulting residue was coevaporated twice with 10 mL n-heptane each time. The residue was then taken up in 10 mL of DCM, treated with 0.94 g of NEt$_3$, 3 g of molecular sieve and 1.3 g of tetrabutylammonium iodide and subsequently reacted with 5.50 g of compound II-2 from preparation example 4 at 40° C. for 64 h. After filtration on silica gel with EE/CHE 1:1 v/v, 2.1 g of the title compound were obtained (yield 64% of theory).

Example 6: Preparation of the Compound of the Formula IIIb, where $R^2$=CH$_3$ and $R^3$=CH$_3$ and $R^4$=H In a manner analogous to example 3, 1.5 g (3.3 mmol) of tetrakistrimethylsilylfucose were firstly stirred with 3.27 g of a 29% strength by weight solution of trimethylsilyl iodide in DCM for 20 min. The reaction solution was then added to 0.45 g of NEt$_3$, 0.12 g of tetrabutylammonium iodide and 1.8 g (3.1 mmol) of compound II-2 from preparation example 4 in 12 mL of DCM and the mixture was reacted at 40° C. for 24 h. 10 mL of methanol were then added to the reaction mixture which was stirred for 30 minutes at RT and then treated with 50 mg of K$_2$CO$_3$ and stirred for a further 3 h. After dilution of the resulting mixture with 20 mL of DCM, the organic phase was separated, washed with saturated aqueous NaHCO$_3$ solution and subsequently evaporated to dryness. Filtration of the residue on silica gel with a gradient of CHE/EE 100/0→CHE/EE/MeOH 0/80/20 afforded 163 mg of the title compound.

$^{13}$C NMR (CD$_2$Cl$_2$, 500 MHz): δ(ppm) 111.03, 110.03, 109.02, 108.03, 101.85, 97.15, 80.74, 78.44, 77.78, 76.26, 75.64, 75.10, 75.01, 74.54, 72.52, 71.43, 69.81, 66.73, 65.47, 62.61, 57.92, 54.37, 28.11, 27.30, 26.96, 26.94, 26.55, 25.04, 16.69.

Example 7: Preparation of 2'-O-fucosyllactose 0.3 g of compound IIIc from example 5 in 3 mL of MeOH was stirred with 0.3 mL of water and 2.3 eq. of K$_2$CO$_3$ at RT for 16 h. The HPLC chromatogram shows 98% of the compound IIIb where $R^2$=$R^3$=CH$_3$ and $R^4$=H, which was identified by its retention time Rt=3.46 min. and by spiking with a sample from example 6. To this were then added 9 g of a 60% by weight aqueous acetic acid solution and the mixture was stirred at 60° C. for 23 h, until complete conversion had been achieved according to HPLC.

After evaporation of the reaction mixture and filtration of the residue on silica gel with chloroform/methanol 8/2, 54 mg of 2'-O-fucosyllactose were obtained, which was identified by its retention time in the HPLC (Rt=8.16 min.) and by comparison with commercially available 2'-O-fucosyllactose.

$^{13}$C as mixture of the anomeric α-isomers

Isomer I $^{13}$C NMR (D$_2$O, 500 MHz): δ(ppm) 103.08, 102.17, 98.75, 79.11, 78.57, 78.16, 78.07, 77.15, 76.76, 76.44, 74.51, 72.45, 71.99, 70.99, 69.76, 63.98, 63.00, 18.13.

Isomer II $^{13}$C NMR (D$_2$O, 500 MHz): δ (ppm) 103.04, 102.17, 94.66, 79.12, 78.69, 78.07, 76.44, 74.51, 74.16, 74.11, 73.22, 72.45, 72.02, 70.99, 69.79, 64.01, 62.87, 18.10.

Example 8: Preparation of 2'-O-Fucosyllactose 0.3 g of compound IIIc from example 5 was stirred in 7 mL of 0.5% aqueous HCl for 24 h.

According to HPLC, the compound IIIc was converted quantitatively to 2'-O-fucosyllactose, which was identified by its identical retention time to example 7.

Example 9: Preparation of the Compound of the Formula IIIa, where $R^{1a}$=CH$_3$, $R^2$=CH$_3$, $R^3$=CH$_3$, and $R^4$=Si(CH$_3$)$_3$ a) 3.4 g of tetrakistrimethylsilylfucose (compound of formula (I) where $R^{Si}$=Si(CH$_3$)$_3$, 92% strength, 6.9 mmol) were dissolved in 10 mL of DCM, then 1.38 g (6.9 mmol) of TMSI were added dropwise and the reaction mixture was stirred for 20 min. Then, the volatile constituents were removed in vacuo at 40° C. and the residue was codistilled twice with 10 mL of toluene each time. The crude product was taken up in 10 mL of DMF.

b) In a second flask, a suspension of 3.4 g of molecular sieve (4 Angstrom) previously heated in vacuo, 0.11 g (0.7 mmol) of KI, 0.18 g (0.7 mmol) of I$_2$, 0.92 g (9.1 mmol) of NEt$_3$ and 5.7 g (10.4 mmol, 1.3 eq.) of compound II-2 from preparation example 4 in 7.8 g of DMF was heated at 50° C. Then, the solution of tris(trimethylsilyl)fucosyl iodide in DMF from step a) was added dropwise and the mixture was stirred for 24 h at 50° C.

Insoluble constituents of the mixture were filtered off and the volatile constituents were removed in vacuum to afford 13.8 g of a crude product with a product content of 32.3% (according to the quantitative HPLC analysis). Crude yield: 77.3% of theory.

The crude product was further purified by chromatography on silica gel (1000 mL) with a gradient of cyclohexane/ethyl acetate 2:1 with 1% $NEt_3$ → cyclohexane/ethyl acetate 1:1 with 1% $NEt_3$ to afford 5.1 g of the title compound with a purity of 95% (according to on HPLC method; 10.3 min).

Example 10: Preparation of the Compound of Formula IIIc, where $R^{11}=CH_3$, $R^2=CH_3$, $R^3=CH_3$, and $R^4$=trimethylsilyl a) 1.08 g (7.2 mmol) of hexamethyldisilane (98% strength) and 1.86 g (7.2 mmol) of iodine (98% strength) were heated at 65° C. and the mixture was hold at this temperature until the decay of the exothermic reaction. The reaction mixture was slowly heated until reflux at about 110° C. and stirred for 90 min. The reaction mixture was cooled to RT. Then, 3.58 g (7.2 mmol) of tetrakistrimethylsilylfucose (92% strength) in 2 mL of DCM were added and the reaction mixture was stirred for 20 min. The volatile constituents were removed in vacuum at 40° C. and the residue was codistilled three times with 10 mL of toluene each time. The residue was taken up in 10 mL of DCM.

b) In a second flask, a suspension of 3.4 g molecular sieve (4 Angström) previously heated in vacuo, 0.053 g (0.36 mmol) of NaI, 0.091 g (0.36 mmol) of $I_2$, 0.95 g (9.4 mmol) of triethylamine and 3.97 g (7.2 mmol, 1 eq.) of the compound of formula II-2 from preparation example 4 in 3.5 g of DCM was heated at 50° C. and the solution of the iodine-containing fucose building block from step a) was added dropwise and the mixture was stirred for 24 h at 50° C.

Insoluble constituents were filtered off and the volatile constituents were removed in vacuum to afford 8.1 g of a crude product comprising 59.6% by weight of the title compound (yield: 78%).

For the work-up, the crude product was again taken up in 10 mL of DCM and washed with 10 mL of 10% sodium thiosulfate solution. After evaporation in vacuo, 6.6 g of crude compound comprising 71.6% by weight of the title compound were obtained.

In a manner analogous to example 9, the crude title compound was purified by chromatography on silica gel to afford 4.8 g of the title compound with a purity of 99% (yield: 75.8%, HPLC method 2: 10.3 min).

Example 11: Preparation of the Compound of the Formula IIIc where $R^{11}=CH_3$, $R^2=CH_3$, $R^3=CH_3$, and $R^4$=trimethylsilyl a) 2.02 g (13.5 mmol) of hexamethyldisilane (98% strength) and 3.47 g (13.5 mmol) of iodine (98% strength) were stirred in 4.2 g of DCM for 180 min at RT and then 11 g (22.5 mmol) tetrakistrimethylsilylfucose (92.8% strength) in 4.2 g of DCM were added. After 180 min stirring at RT, the volatile constituents were removed at 40° C. in vacuo and the residue was codistilled three times with 10 mL of toluene each time. Then, the crude product was taken up in 3.8 mL of DCM.

b) In a second flask, a suspension of 0.169 g (1.1 mmol) of NaI, 2.96 g (29.3 mmol) of $NEt_3$ and 12.42 g (22.5 mmol, 1 eq.) of compound II-2 from preparation example 4 in 10 g of DCM was prepared and the solution of the iodine-containing fucose building block from step a) was added dropwise. After heating to an internal temperature of 50-64° C. for 24 h, the mixture was cooled and the insoluble constituents were filtered off. Then, the filtrate was diluted with 13.4 g of DCM and washed with 10% sodium thiosulfate solution (14 g).

After concentration, 21.7 g of crude product comprising 72.5% by weight of the title compound (according to HPLC method 2: 10.3 min) were obtained.

Example 12: Preparation of the Compound of the Formula IIIc where $R^{11}=C(CH_3)_3$, $R^2=CH_3$, $R^3=CH_3$, and $R^4$=trimethylsilyl 3.33 g (13.1 mmol) of iodine and 1.94 g (13.1 mmol) of hexamethyldisilane in 3 mL of DCM were stirred for 3 h at RT. To this were added 11 g (21.6 mmol) of a 89% strength tetrakistrimethylsilylfucose ( ) in 3 mL of DCM and stirring was continued for further 20 min at RT. Volatile constituents were removed in vacuo at 40° C. and 30 mbar and the residue was coevaporated three times with 10 mL of toluene each time. The residue was dissolved in 1 mL of DCM.

To a under reflux heated mixture of 2.84 g (28 mmol) of triethylamine, 0.16 g (1.1 mmol) of NaI, 12.81 g (21.6 mmol) of compound II-4 from preparation example 6 in 7.5 g of DCM was added dropwise this solution. Then, the reaction mixture was heated under reflux for 20 h under stirring. For the work-up, 10 mL of 10% sodium thiosulfate solution were added, the mixture was vigorously stirred for 5 min and the phases were separated. The organic phase was washed with 5 mL of water, dried over $Na_2SO_4$ and concentrated.

For characterization and purification, 17.0 g of the crude product were dissolved in cyclohexane/ethyl acetate 5:1, treated with 1% triethylamine and transferred onto the top of a silica gel column (dimension of the column: diameter d=9 cm, height h=37 cm, volume V~2.3 L). The column was eluted under slight pressure. Product fractions were combined and concentrated at 45° C. and 5 mbar by means of rotary evaporation and then for 1 h by means of oil pump vacuo to afford 11.42 g of the title compound.

$^{13}C$ NMR ($CD_2Cl_2$, 500 MHz): δ(ppm) 178.18, 110.26, 110.12, 108.96, 105.84, 101.80, 97.96, 80.26, 78.01, 77.56, 76.29, 75.94, 75.37, 75.23, 73.80, 71.23, 70.96, 69.25, 66.98, 65.98, 62.78, 56.23, 53.40, 39.01, 27.92, 27.41, 27.32, 27.27, 27.27, 27.27, 27.16, 26.35, 25.66, 17.08, 0.77, 0.77, 0.77, 0.62, 0.62, 0.62, 0.26, 0.26, 0.26.

Example 13: Preparation of the Compound of the Formula IIIc where $R^{11}=C(CH_3)_3$, $R^2=CH_3$, $R^3=CH_3$, and $R^4$=trimethylsilyl a) 7.08 g (14 mmol) of 89.4% by weight strength tetrakistrimethylsilylfucose were dissolved in 4 mL of DCM and treated with 2.88 g (13.5 mmol) of TMSI (97%). After stirring for 20 min, the volatile constituents were removed in vacuo and then the residue was codistilled three times with 10 mL of toluene each time. The crude product was taken up in 2 mL of DCM.

b) In a second flask, 8.28 g (14 mmol) of compound II-4 from preparation example 6 in 4 g of DCM were treated with 1.86 g of triethylamine (1.3 eq. based on fucose building block), 105 mg of NaI (0.05 eq. based on fucose building block) and 0.177 g of iodine (0.05 eq. based on fucose building block) and subsequently the solution of trimethylsilylfucose iodide from step a) was added dropwise at 50 to 65° C. After stirring and heating under reflux for further 24 h, the mixture was cooled and the insoluble constituents were filtered off.

The organic phase was subsequently washed with 10 mL of 10% sodium thiosulfate solution and 10 mL of water and then dried over $Na_2SO_4$.

After filtration and concentration, 13.5 g of crude product comprising 69.5% by weight of the title compound (71% yield, according to HPLC method 2: 15.04 min) were obtained.

Example 14: Preparation of the Compound of the Formula IIIc where $R^{11}$=C(CH$_3$)$_3$, $R^2$=CH$_3$, $R^3$=CH$_3$, $R^4$=trimethylsilyl 1.28 g (8.7 mmol) of hexamethyldisilane (98%) and 2.2 g (8.7 mmol) of iodine (98%) were stirred in 2 mL of DCM for 180 min at RT. To this were added 8 g (14.3 mmol) of tetrakistrimethylsilylfucose (81% strength) in 1 mL of DCM. After stirring for 180 min at RT, 0.573 g (5 mmol) KHCO$_3$ were added and the mixture was stirred for 60 min at RT. 1.88 g (18.6 mmol) of triethylamine were then added and the mixture was heated under reflux. 15.92 g of a 53% by weight dichloromethane solution of the compound II-4 from preparation example 6 (14.3 mmol) were added and the mixture was heated under stirring and reflux for 24 h.

After cooling, the insoluble constituents were filtered off and the filtrate was subsequently washed with 10 g of a 10% sodium thiosulfate solution and water. After drying over Na$_2$SO$_4$ and concentration to dryness, 16 g of a crude product comprising 61.5% by weight of the title compound (according to HPLC method 2) (crude yield: 71.5%) were obtained.

Example 15: One-Pot Reaction for the Preparation of 2'-O-fucosyllactose 1.28 g of hexamethyldisilane (8.7 mmol) and 2.2 g of iodine (8.7 mmol) in 2 mL of DCM were stirred for 3 h at RT. 7.25 g (14.3 mmol) of tetrakistrimethylsilylfucose (89.4% strength) were then added and the mixture was stirred for 20 min. The volatile constituents were removed in vacuo and the residue was evaporated three times with 10 mL of toluene each time. The residue was dissolved in 1.4 mL of toluene and added dropwise to a solution of 1.88 g (18.6 mmol) of triethylamine, 0.107 g (0.7 mmol) of NaI and 8.47 g of compound II-4 from preparation example 6 in 5.4 g of DCM, the solution being heated under reflux. The mixture was stirred and heated under reflux for 24 h, filtered and concentrated.

The residue was dissolved in about 10 mL of DCM and washed with 10 mL of 10% sodium carbonate solution and 10 mL of 10% sodium thiosulfate solution. The combined aqueous phases were extracted with 6 mL of DCM. The combined organic phases were dried over Na$_2$SO$_4$ and concentrated to afford 13.9 g of crude product IIIc where $R^{11}$=C(CH$_3$)$_3$, $R^2$=CH$_3$, $R^3$=CH$_3$ and $R^4$=Si(CH$_3$)$_3$.

13.8 g of the obtained crude product IIIc in 44.8 mL of methanol were treated with 2.82 g (20 mmol) of K$_2$CO$_3$ and stirred for 16 h. Methanol was distilled off at 300 mbar until the temperature was 38° C. Then, 28 mL of DCM were added and the mixture was washed with 13.5 mL of water. The aqueous phase was reextracted with 6.6 mL of DCM and the combined organic phases were dried over Na$_2$SO$_4$. After removal of the solvent, the crude product was checked for complete conversion by means of HPLC analysis and then taken up in 28 mL of DCM. To this were added 28 mL of water and DCM was distilled off. Then 6.6 mL of water and 34.8 mL of 1 N HCl were added and the mixture was stirred for 24 h at RT.

Subsequently, the mixture was neutralized by elution through a column charged with 53 mL of ion exchanger IMAC HP 661 followed by rewashing with 26 mL of water and the combined aqueous phases were rewashed with 6 mL of DCM. After evaporation in vacuo, 6.2 g of the crude product with 67.2% by weight of 2'-O-fucosyllactose (HPLC method 2) were obtained. The ratio of the target (1-2-α) product to (1-2-ß) product was 29:1 (area percent).

Example 16: Preparation of the Compound of the Formula IIIc where $R^1$=C(CH$_3$)$_3$, $R^2$=CH$_3$, $R^3$=CH$_3$, and $R^4$=Si(CH$_3$)$_3$ 17.97 g (0.120 mol) of hexamethyldisilane and 30.84 g of iodine (0.120 mol) in 30 mL of DCM were stirred for 3 h at RT. 102.3 g of tetrakistrimethylsilylfucose (89% by weight, 0.205 mol) were added and the mixture was stirred for 20 min at RT. The volatile constituents were removed in vacuo and the residue was codistilled three times with 75 mL of toluene each time.

The thus obtained crude tris(trimethylsilyl)fucosyl iodide was added dropwise to a solution of 118.83 g of compound II-4 from preparation example 6, 26.38 g (0.2607 mol) of triethylamine and 1.5 g of NaI (0.01 mol) in 75 g of DCM, the solution being heated under reflux, followed by rinsing with 30 mL of DCM. After heating under reflux for 24 h, the reaction mixture was cooled to RT, 150 mL of DCM and 200 mL of 5% sodium thiosulfate solution were added and the mixture was vigorously stirred for 10 min. The organic phase was separated, washed with 50 mL of water, dried over Na$_2$SO$_4$, filtered and concentrated. According to HPLC analytics, 76.7% of the title product were obtained.

The crude product was divided into two portions of each 100 g and both portions were purified by column chromatography on silica gel (column: diameter d=12.5 cm, height h=40 cm, volume V~4.9 L) using cyclohexane/ethyl acetate 5:1 and 1% of triethylamine, to afford 70.9 g of a product fraction with a purity of 94.6% (first column) and 71.9 g with a purity of 87.5% (second column). Both product fractions were combined.

Example 17: Preparation of the Compound of Formula IIIb where $R^2$=CH$_3$, $R^3$=CH$_3$ and $R^4$=Si(CH$_3$)$_3$ 155.38 g of compound IIIc where $R^{11}$=C(CH$_3$)$_3$, $R^2$=CH$_3$, $R^3$=CH$_3$, $R^4$=Si(CH$_3$)$_3$ (content 85.7% by weight, prepared according to Example 16), were stirred in 569 mL of MeOH with 38.5 g K$_2$CO$_3$ for 22 h at RT. The volatile constituents were removed in vacuo and the residue was taken up in 350 mL of DCM and washed three times with 150 mL of water each time. The combined aqueous phases were reextracted once with DCM and the combined organic phases were dried over Na$_2$SO$_4$. After filtration and concentration in vacuo, 118.2 g of the crude product IIIb with a content of 90.4% were obtained.

For easy handling for further reactions, the crude product was dissolved in 100 mL of DCM.

Example 18: Preparation of 2'-O-fucosyllactose 125 g of the crude product solution from Example 17 (59.1 g of compound IIIb in DCM) were treated with 175 mL of water and DCM was distilled off at 50° C. and 400 mbar by means of a rotary evaporator. The aqueous mixture was cooled to RT, further 191 mL of water and 122 mL of 2N HCl (corresponding to a total concentration of HCl of 0.5 mol/L) were added and stirred over night at RT. Then the solution (535 g) was filtered through a weakly basic ion exchanger Lewatit MP62 followed by rewashing three times with 160 mL of water each time. The mother liquor and the washing liquors were combined and evaporated at 300° C. and 5 mbar by means of a rotary evaporation and 1 h by means of an oil pump vacuo to afford 38.9 g of product with a purity of 90.7%; the product content was 78.3% by weight (according to HPLC method 3). The ratio of the target (1-2-α) product to (1-2-ß) product was 49:1 (percent by weight).

Example 19: Preparation of 2'-O-fucosyllactose

In a manner analogous to Example 18, 25 g of the solution of the compound IIIb in DCM obtained in Example 17 were treated with aqueous hydrochloride acid and then filtered through 80 mL of Amberlyst A21 to afford 8.05 g of 2'-O-fucosyllactose with a purity of 88.7%, based on the constituents different from lactose. The content of 2'-O-fucosyllactose was 72% by weight.

Example 20: Preparation of 2'-O-Fucosyllactose

In a manner analogous to Example 18, 25 g of the solution of the compound IIIb in DCM obtained in Example 17 were treated with aqueous hydrochloride acid and then filtered through IMAC HP 661 to afford 7.7 g of a crude product with a purity of 91.1%, based on the constituents different from lactose. The content of 2'-O-fucosyllactose was 78% by weight.

5.0 g of 2'-O-fucosyllactose were dissolved in 15 mL of MeOH in the heat and the insoluble constituents were filtered off in the heat. The title product was precipitated from the filtrate by adding 45 mL of cold EtOH, the precipitate was filtered off and washed two times with EtOH. The title product was obtained with a purity of 92%, the purity being determined without lactose. The yield was 78.8%.

HPLC: 0.05% by weight of fucose; 8.9% by weight of lactose; 0.2% by weight of 2'-FI 3-anomer; 69.0% by weight of 2'-FI; 1.75 area-% of tetrasaccharide Purification 1: Purification of 2'-O-Fucosyllactose Using Methanol:

5.0 g of the crude product of 2'-O-fucosyllactose from Example 18 in 35 mL of MeOH were heated under reflux and the suspension was concentrated to a total volume of 10 mL. The mixture was then cooled to −5° C. and stirred for 30 min. The obtained solids were sucked off and washed two times with 2 mL of cold methanol each time and two times with 2 mL of cold acetone each time. 3.41 g of the title product in a yield of 83.7% by weight were obtained.

The title product contained 11.5% by weight of lactose, the purity was 97.4 area-% according to HPLC method 3 and under taking into account the lactose content.

Purification 2: Purification of 2'-O-Fucosyllactose Using $H_2O$/Acetone:

5.0 g of 2'-O-fucosyllactose from Example 18 were dissolved in 3 mL of water at 75° C. Then, the solution was cooled, 1 mL of acetone and 5 mL of EtOH were added and the mixture was stirred for 16 h. The mixture was filtered and the obtained solids were washed three times with 3 mL of EtOH/$H_2O$ (96.5:3.5) each time. 2.14 g of the title product (yield: 50.0%) were obtained. The content of lactose was 12% according to HPLC analysis.

Example 21 (Comparison Example): Preparation of the Comparison Compound, ß-Isomer of 2'-FL (2'-O-α-L-fucopyranosyllactose)

2,3,4-Tri-O-acetyl-ß-L-fucopyranosyltrichloroacetimidate was prepared as outlined in Liebigs Ann Chemie, 1991, 121.

Step 1: O-(2,3,4-Tri-O-acetyl-ß-L-fucopyranosyl)-(1-2)-O-(6-O-acetyl-3,4-isopropylidene-ß-D-galactopytanosyl)-(1-4)-2,3:5,6-di-O-isopropylidene-D-glucose-dimethylacetal A flask charged with 1.5 g of molecular sieve 4 Å was heated in vacuo and purged with argon. To this was added a solution of 2.77 g (5 mmol) of compound II-2 from preparation example 4 in 2 g of $CH_2Cl_2$ and then 1.46 g (3.3 mmol) of 3,4-tri-O-acetyl-ß-L-fucopyranosyltrichloroacetimidate at −5-0° C. and the mixture was stirred for 1 h at 0° C. Then, 48 mg of $BF_3.OEt_2$ in 1 mL of $CH_2Cl_2$ were added dropwise at 0 bis 5° C. and the mixture was stirred for 6 h at 0° C. and then over night at 0 to 20° C. The reaction mixture was filtered and washed with 10 mL of $CH_2Cl_2$. The combined organic phases were washed with 10 mL of saturated $NaHCO_3$ solution, dried over $Na_2SO_4$, filtered and concentrated. 3.85 g of crude product were obtained which were purified by chromatography on silica gel (500 mL) with cyclohexane/ethyl acetate 2:1 to 1:1 to afford 1 g of the title compound.

$^{13}C$ NMR ($CD_2Cl_2$, 500 MHz): δ(ppm) 170.97, 170.97, 170.45, 170.01, 110.45, 110.16, 109.00, 106.11, 101.69, 99.96, 78.01, 77.96, 77.76, 76.94, 75.54, 75.50, 73.87, 72.05, 71.17, 70.68, 69.72, 69.53, 66.60, 63.46, 56.18, 53.69, 27.90, 27.50, 27.16, 27.06, 26.39, 25.75, 21.17, 21.02, 20.93, 20.84, 16.00.

Step 2: O-ß-L-fucopyranosyl-(1-2)-O-(3,4-isopropylidene-ß-D-galactopytanosyl)-(1-4)-2,3:5,6-di-O-isopropylidene-D-glucose-dimethylacetal 1.87 g of the compound from step 1 were treated with 10 mL of methanol and 406 mg of sodium methylate for 16 h at RT under stirring. Then, insoluble constituents were filtered, the mixture was concentrated in vacuo and purified by chromatography on 100 mL of silica gel with dichloromethane/MeOH 95:5 to afford 1.1 g of the title compound.

$^{13}C$ NMR ($CD_2Cl_2$, 500 MHz): δ(ppm) 110.37, 110.21, 108.53, 107.61, 103.24, 102.57, 79.02, 78.93, 78.64, 78.24, 75.54, 74.95, 74.85, 74.40, 74.18, 72.06, 71.57, 70.94, 64.63, 62,46. 57.82, 54.25, 28.07, 27.27, 26.55, 26.46, 26.05, 23.64, 16.28.

Step 3: ß-2'-O-Fucosyllactose 0.97 g of the product from step 2 were treated with 21.6 mL of aqueous hydrochloride acid (0.5 M) and stirred for 20 h at RT. Then, the reaction mixture was neutralized with 7.8 mL of ion exchanger IMAC HP661, filtered and washed with 10 mL of water. After removal of the volatile constituents in vacuo, the residue was dried under high vacuo, 0.66 g of the (R-isomer of 2'-O-fucosyllactose as a mixture of the anomers at the reducing end groups were obtained.

Anomer I $^{13}$C NMR (CD$_3$OD, 500 MHz): δ(ppm) 104.48, 102.56, 98.11, 80.55, 78.93, 77.03, 76.97, 76.16, 75.22, 73.85, 73.81, 73.09, 72.63, 72.22, 69.77, 62.72, 62.26, 16.78;

Anomer II $^{13}$C NMR (CD$_3$OD, 500 MHz): δ(ppm) 104.40, 102.68, 93.80, 80.37, 79.34, 76.97, 76.10, 75.18, 73.70, 73.11, 72.92, 72.62, 72.22, 71.83, 69.74, 62.73, 62.27, 16.78.

The invention claimed is:

1. A method for preparing 2'-O-fucosyllactose, comprising:
a) reacting protected fucose of formula (I)

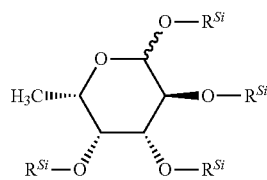

(I)

where each $R^{Si}$ is the same or different and is a residue of the formula $SiR^aR^bR^c$, where $R^a$, $R^b$ and $R^c$ are the same or different and are selected from the group consisting of $C_1$-$C_8$-alkyl, $C_3$-$C_8$-cycloalkyl, phenyl and $C_3$-$C_8$-cycloalkyl-$C_1$-$C_4$-alkyl;
with a compound of formula (II)

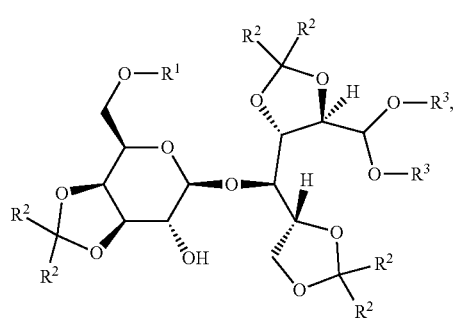

(II)

where
$R^1$ is a C(=O)—$R^{11}$ residue or an $SiR^{12}R^{13}R^{14}$ residue, in which
$R^{11}$ is hydrogen, $C_1$-$C_8$-alkyl, $C_1$-$C_8$-haloalkyl, $C_3$-$C_8$-cycloalkyl, $C_3$-$C_8$-cycloalkyl-$C_1$-$C_4$-alkyl or phenyl, wherein said phenyl is unsubstituted or has 1 to 5 substituents selected from the group consisting of halogen, CN, NO$_2$, $C_1$-$C_4$-alkyl, $C_1$-$C_4$-alkoxy, $C_1$-$C_4$-haloalkyl and $C_1$-$C_4$-haloalkoxy, and
$R^{12}$, $R^{13}$ and $R^{14}$ are the same or different and are selected from the group consisting of $C_1$-$C_8$-alkyl, $C_3$-$C_8$-cycloalkyl, phenyl and $C_3$-$C_8$-cycloalkyl-$C_1$-$C_4$-alkyl;
$R^2$ is each the same or different and are $C_1$-$C_8$-alkyl or 2 $R^2$ residues attached to the same carbon atom together form a linear $C_3$-$C_6$-alkanediyl, which is unsubstituted or has 1 to 6 methyl groups as substituents;

$R^3$ is each the same or different and are $C_1$-$C_8$-alkyl or together form a linear $C_1$-$C_4$-alkanediyl, which is unsubstituted or has 1 to 6 methyl groups as substituents;
b) deprotecting the coupling product of the general formula (III) obtained in step a)

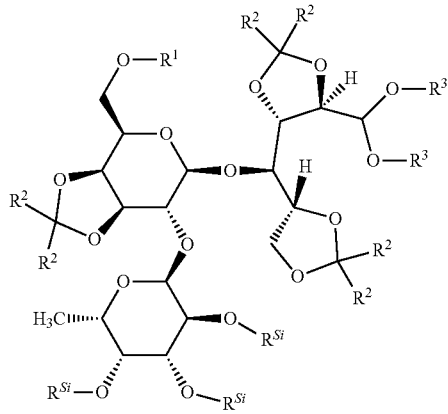

(III)

where $R^{Si}$, $R^1$, $R^2$ and $R^3$ are as defined above;
to obtain 2'-O-fucosyllactose;
wherein step a) comprises
a.1) treating the protected fucose of formula (I) with a tri($C_1$-$C_6$-alkyl)silyl iodide
a.2) reacting the product obtained in step a.1) with the compound of the formula (II) in the presence of at least one base;
wherein the compound of formula (I) and the compound of formula (II) are reacted in a molar ratio (I):(II) in the range of 1:3 to 2:1.

2. The method according to claim 1, wherein the tri($C_1$-$C_6$-alkyl)silyl iodide is trimethylsilyl iodide.

3. The method according to claim 1, wherein the tri($C_1$-$C_6$-alkyl)silyl iodide is used in an amount of 0.8 to 1.4 mol per mole of the compound of the formula (I).

4. The method according to claim 1, wherein the tri($C_1$-$C_6$-alkyl)silyl iodide is generated in situ by treatment of the corresponding tri($C_1$-$C_6$-alkyl)silyl chloride with an iodide salt.

5. The method according to claim 1, where the tri($C_1$-$C_6$-alkyl)silyl iodide is generated in situ by reacting the corresponding hexa($C_1$-$C_6$-alkyl)disilane with iodine.

6. The method according to claim 5, wherein, first, in step a.1) the hexa($C_1$-$C_6$-alkyl)disilane is reacted with iodine and then the resulting reaction mixture is reacted with the compound of formula (I).

7. The method according to claim 1, wherein in step a):
a.1) the compound of the formula (I) is first treated with a tri($C_1$-$C_6$-alkyl)silyl iodide and
a.2) the resulting product is reacted without further purification with the compound of the formula (II) in the presence of the base.

8. The method according to claim 5, wherein the base is used in at least an equimolar amount, based on the compound of the formula (I).

9. The method according to claim 5, wherein the base comprises at least one basic compound, which is selected from amine bases.

10. The method according to claim 9, wherein, the base additionally comprises a basic compound, which is selected from the group consisting of alkali carbonates, alkali hydrogen carbonate and mixtures thereof.

11. The method according to claim 10, wherein,
   a.1) first, the hexa($C_1$-$C_6$-alkyl)disilane is reacted with iodine and then the resulting reaction mixture is reacted with the compound of formula (I);
   a.2) the reaction mixture of step a.1) is treated with a basic compound, which is selected from the group consisting of alkali carbonates, alkali hydrogen carbonate and mixtures thereof, and the resulting mixture is subsequently reacted with the compound of formula (II) in the presence of an amine base.

12. The method according to claim 5, wherein step a.2) takes place in the presence of at least one reagent selected from the group consisting of iodine, iodide salts and triarylphosphine oxides and mixtures thereof.

13. The method according to claim 1, wherein in step b)
   b.1) the compound of the formula (III) is treated with water in the presence of an acid;
   or
   b.2) the compound of the formula (III), in which $R^1$ is an $SiR^{12}R^{13}R^{14}$ residue, is first treated with a desilylating reagent, wherein a compound of formula (IIIb') is obtained:

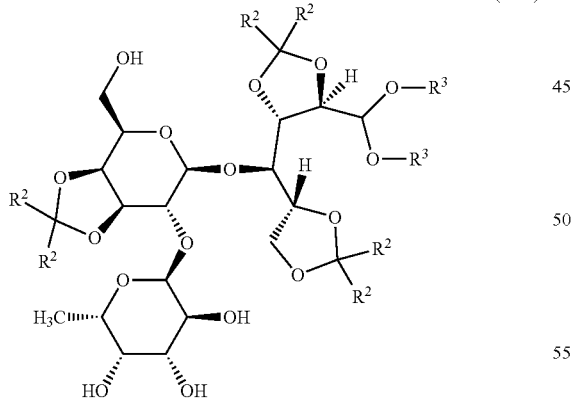

(IIIb')

and subsequently the remaining protecting groups are removed by treating the compound of the formula (IIIb') with water in the presence of an acid;
or
   b.3) the compound of the formula (III), in which $R^1$ is a $C(O)R^{11}$ residue, is first treated with a desilylating reagent, wherein a compound of the formula (IIIc') is obtained:

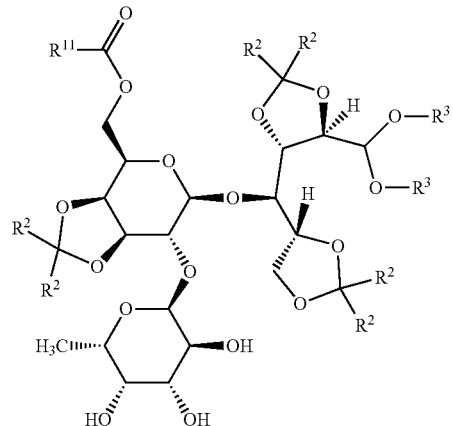

(IIIc')

and subsequently the C(O)—$R^{11}$ group and the remaining protecting groups are successively removed;
or
   b.4) the protecting groups $C(R^2)_2$ and $OR^3$ are first removed from the compound of the formula (III), in which $R^1$ is a $C(O)R^{11}$ residue, wherein a compound of the formula (IV) is obtained:

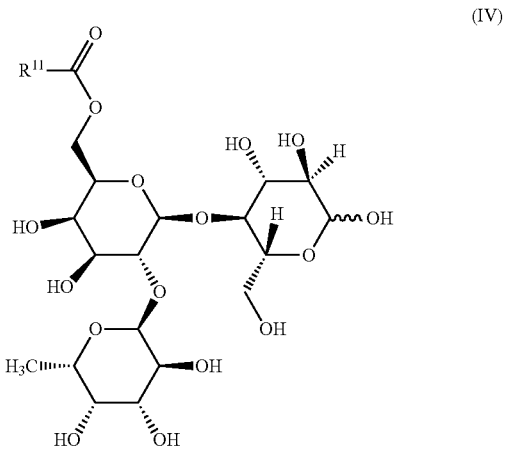

(IV)

and the C(O)—$R^{11}$ group is subsequently removed,
or
   b.5) the compound of formula (III), wherein $R^1$ is a radical C(O)—$R^{11}$, is first treated with a $C_1$-$C_4$-alkanol and an alkalimetal base, whereby a compound of formula (IIIb') is obtained, and subsequently the remaining protecting groups are removed by treating the compound of the formula (IIIb') under acidic reaction conditions.

14. The method according to claim 1, wherein the $R^{Si}$ residue in formulae (I) and (III) is trimethylsilyl.

15. The method according to claim 1, wherein the $R^1$ residue in formulae (II) and (III) is trimethylsilyl.

16. The method according to claim 1, wherein the $R^1$ residue in formulae (II) and (III) is acetyl, pivaloyl or benzoyl.

17. The method according to claim 1, wherein the $R^2$ residue in formulae (II) and (III) is methyl.

18. The method according to claim 1, wherein the $R^3$ residue in formulae (II) and (III) is methyl.

19. A compound of formula (IIIa)

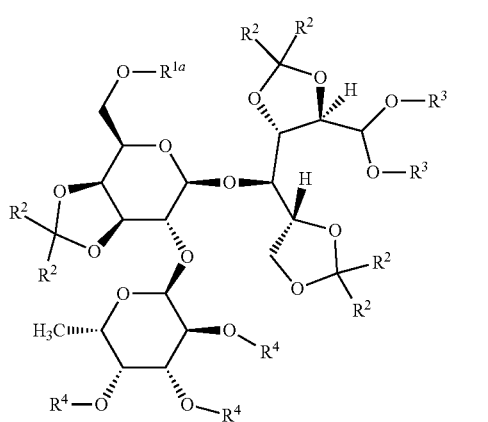

(IIIa)

where $R^{1a}$ is an $SiR^{12}R^{13}R^{14}$ residue residue, where $R^{12}$, $R^{13}$ and $R^{14}$ are the same or different and are selected from the group consisting of $C_1$-$C_8$-alkyl, $C_3$-$C_8$-cycloalkyl, phenyl and $C_3$-$C_8$-cycloalkyl-$C_1$-$C_4$-alkyl;

$R^2$ are the same or different and are $C_1$-$C_8$-alkyl or 2 $R^2$ residues attached to the same carbon atom together form a linear $C_3$-$C_6$-alkanediyl, which is unsubstituted or has 1 to 6 methyl groups as substituents;

$R^3$ are the same or different and are $C_1$-$C_8$-alkyl or together form a linear $C_1$-$C_4$-alkanediyl, which is unsubstituted or has 1 to 6 methyl groups as substituents;

$R^4$ are the same or different and are hydrogen or an $SiR^aR^bR^c$ residue, where $R^a$, $R^b$ and $R^c$ are the same or different and are selected from the group consisting of $C_1$-$C_8$-alkyl, $C_3$-$C_8$-cycloalkyl, phenyl and $C_3$-$C_8$-cycloalkyl-$C_1$-$C_4$-alkyl.

20. A compound of formula (IIIb)

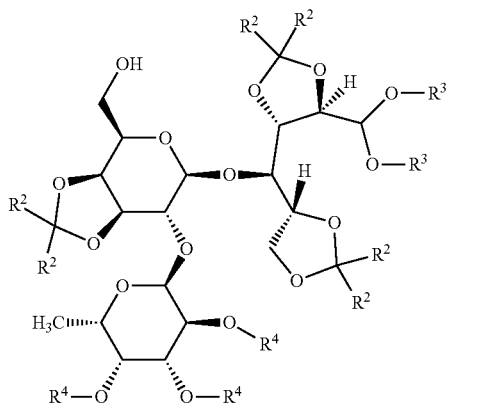

(IIIb)

where $R^2$ are the same or different and are $C_1$-$C_8$-alkyl or 2 $R^2$ residues attached to the same carbon atom together form a linear $C_3$-$C_6$-alkanediyl, which is unsubstituted or has 1 to 6 methyl groups as substituents;

$R^3$ are the same or different and are $C_1$-$C_8$-alkyl or together form a linear $C_1$-$C_4$-alkanediyl, which is unsubstituted or has 1 to 6 methyl groups as substituents;

$R^4$ are the same or different and are hydrogen or an $SiR^aR^bR^c$ residue residue, where $R^a$, $R^b$ and $R^c$ are the same or different and are selected from the group consisting of $C_1$-$C_8$-alkyl, $C_3$-$C_8$-cycloalkyl, phenyl and $C_3$-$C_8$-cycloalkyl-$C_1$-$C_4$-alkyl.

21. A compound of formula (IIIc)

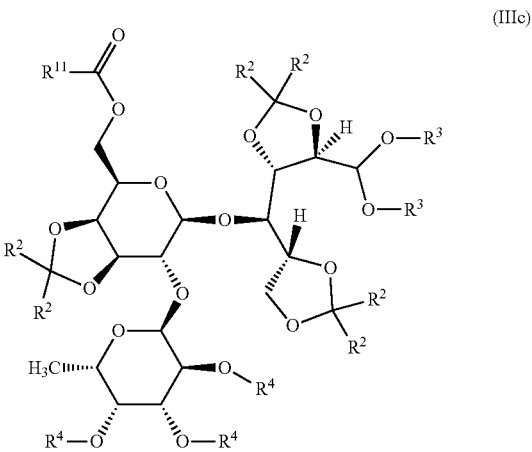

(IIIc)

where $R^{11}$ is hydrogen, $C_1$-$C_8$-alkyl, $C_1$-$C_8$-haloalkyl, $C_3$-$C_8$-cycloalkyl, $C_3$-$C_8$-cycloalkyl-$C_1$-$C_4$-alkyl or phenyl, wherein said phenyl is unsubstituted or has 1 to 5 substituents selected from the group consisting of halogen, CN, $NO_2$, $C_1$-$C_4$-alkyl, $C_1$-$C_4$-alkoxy, $C_1$-$C_4$-haloalkyl and $C_1$-$C_4$-haloalkoxy;

$R^2$ are the same or different and are $C_1$-$C_8$-alkyl or 2 $R^2$ residues attached to the same carbon atom together form a linear $C_3$-$C_6$-alkanediyl, which is unsubstituted or has 1 to 6 methyl groups as substituents;

$R^3$ are the same or different and are $C_1$-$C_8$-alkyl or together form a linear $C_1$-$C_4$-alkanediyl, which is unsubstituted or has 1 to 6 methyl groups as substituents;

$R^4$ are the same or different and are hydrogen or a $SiR^aR^bR^c$ residue, where $R^a$, $R^b$ and $R^c$ are the same or different and are selected from the group consisting of $C_1$-$C_8$-alkyl, $C_3$-$C_8$-cycloalkyl, phenyl and $C_3$-$C_8$-cycloalkyl-$C_1$-$C_4$-alkyl.

22. A compound of formula (IIa)

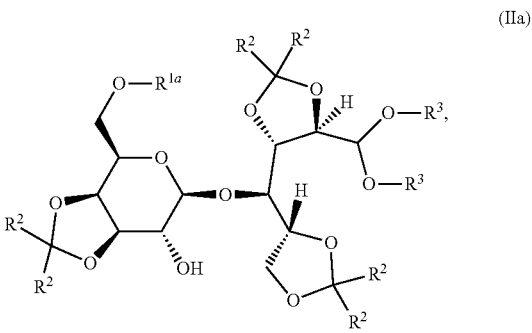

(IIa)

where $R^{1a}$ is an $SiR^{12}R^{13}R^{14}$ residue, where $R^{12}$, $R^{13}$ and $R^{14}$ are the same or different and are selected from the group consisting of $C_1$-$C_8$-alkyl, $C_3$-$C_8$-cycloalkyl, phenyl and $C_3$-$C_8$-cycloalkyl-$C_1$-$C_4$-alkyl;

$R^2$ are the same or different and are $C_1$-$C_8$-alkyl or 2 $R^2$ residues attached to the same carbon atom together form a linear $C_3$-$C_6$-alkanediyl, which is unsubstituted or has 1 to 6 methyl groups as substituents;

and $R^3$ are the same or different and are $C_1$-$C_8$-alkyl or together form a linear $C_1$-$C_4$-alkanediyl, which is unsubstituted or has 1 to 6 methyl groups as substituents, except for the compound of formula (IIa), wherein $R^{1a}$ is tert.butyldimethylsilyl and both $R^2$ and $R^3$ are methyl.

23. A compound of formula (IV)

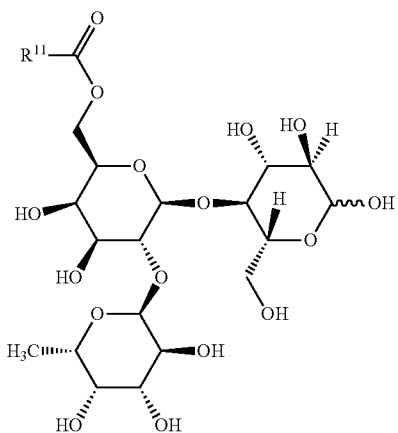

(IV)

where $R^{11}$ is hydrogen, $C_2$-$C_8$-alkyl, $C_1$-$C_8$-haloalkyl, $C_3$-$C_8$-cycloalkyl, $C_3$-$C_8$-cycloalkyl-$C_1$-$C_4$-alkyl or phenyl, wherein said phenyl is unsubstituted or has 1 to 5 substituents selected from the group consisting of halogen, CN, $NO_2$, $C_1$-$C_4$-alkyl, $C_1$-$C_4$-alkoxy, $C_1$-$C_4$-haloalkyl and $C_1$-$C_4$-haloalkoxy.

24. The method according to claim 9, wherein the amine bases are tertiary amines.

25. The method according to claim 1, wherein the base comprises at least one basic compound selected from tri($C_1$-$C_6$-alkyl)amines.

26. The method according to claim 25, wherein the base additionally comprises a basic compound which is an inorganic base selected from the group consisting of alkali carbonates, alkali hydrogen carbonates, and mixtures thereof.

27. The method according to claim 26, wherein tri($C_1$-$C_6$-alkyl)amine is employed in an amount of 1 to 2 mole per mole of the compound of formula (I) and the inorganic base is employed in an amount of 0.005 to 0.25 mole in the case of alkali carbonate and in an amount of 0.01 to 0.5 mole in the case of alkali hydrogen carbonate, each per mole of the compound of formula (I).

28. The method according to claim 1, wherein the $R^1$ residue in formulae (II) and (III) are acetyl.

* * * * *